(12) United States Patent
Wang et al.

(10) Patent No.: US 10,568,541 B2
(45) Date of Patent: Feb. 25, 2020

(54) BREATH ANALYSIS SYSTEMS AND METHODS FOR ASTHMA, TUBERCULOSIS AND LUNG CANCER DIAGNOSTICS AND DISEASE MANAGEMENT

(75) Inventors: Li-Peng Wang, San Jose, CA (US); Chi-Lin Young, San Jose, CA (US); Chien-Lin Huang, Sinjhuang (TW); Tsung-Kuan A. Chou, San Jose, CA (US)

(73) Assignee: TricornTech Taiwan, Taipei (TW)

( * ) Notice: Subject to any disclaimer, the term of this patent is extended or adjusted under 35 U.S.C. 154(b) by 576 days.

(21) Appl. No.: 12/628,126

(22) Filed: Nov. 30, 2009

(65) Prior Publication Data

US 2010/0137733 A1    Jun. 3, 2010

Related U.S. Application Data

(60) Provisional application No. 61/118,977, filed on Dec. 1, 2008.

(51) Int. Cl.
*A61B 5/08* (2006.01)
*A61B 5/097* (2006.01)
*G01N 33/497* (2006.01)
*G01N 30/02* (2006.01)

(52) U.S. Cl.
CPC ............ *A61B 5/08* (2013.01); *A61B 5/082* (2013.01); *A61B 5/097* (2013.01); *G01N 33/497* (2013.01); *G01N 2030/025* (2013.01); *G01N 2033/4975* (2013.01)

(58) Field of Classification Search
CPC .......... G01N 33/497; G01N 2030/025; G01N 2033/4975; A61B 5/097; A61B 5/082

USPC .................................................. 600/529–543
See application file for complete search history.

(56) References Cited

U.S. PATENT DOCUMENTS

| | | | |
|---|---|---|---|
| 4,796,639 A * | 1/1989 | Snow et al. | 600/532 |
| 4,869,876 A | 9/1989 | Arfman et al. | |
| 4,888,295 A | 12/1989 | Zaromb et al. | |
| 5,081,871 A * | 1/1992 | Glaser | 73/863.23 |
| 5,111,827 A | 5/1992 | Rantala | |
| 5,425,374 A | 6/1995 | Ueda et al. | |
| 5,465,728 A | 11/1995 | Phillips | |
| 5,996,586 A | 12/1999 | Phillips | |
| 6,010,459 A * | 1/2000 | Silkoff et al. | 600/532 |
| 6,319,724 B1 | 11/2001 | Lewis et al. | |
| 6,461,306 B1 | 10/2002 | Hanson, III et al. | |

(Continued)

FOREIGN PATENT DOCUMENTS

| | | |
|---|---|---|
| CN | 1954208 | 4/2007 |
| JP | H01-078943 | 5/1988 |

(Continued)

OTHER PUBLICATIONS

Wake Forest University Chem department web page on gas chromatography from 2005.*

(Continued)

*Primary Examiner* — Christian Jang
*Assistant Examiner* — Karen E Toth
(74) *Attorney, Agent, or Firm* — Womble Bond Dickinson (US) LLP

(57) ABSTRACT

Methods and systems are disclosed for the detecting of whether a subject has a lung disorder such as asthma, tuberculosis or lung cancer. Monitoring the subject's health and prognosis is also disclosed.

28 Claims, 16 Drawing Sheets

(56) References Cited

U.S. PATENT DOCUMENTS

| | | | |
|---|---|---|---|
| 6,620,109 B2 | 9/2003 | Hanson, III | |
| 6,723,056 B1 | 4/2004 | Alving et al. | |
| 7,076,371 B2 | 7/2006 | Fu | |
| 7,101,340 B1* | 9/2006 | Braun | 600/532 |
| 7,153,272 B2 | 12/2006 | Talton | |
| 7,172,557 B1* | 2/2007 | Parker | 600/529 |
| 7,255,677 B2 | 8/2007 | Burch et al. | |
| 7,343,779 B1 | 3/2008 | Yu | |
| 7,347,825 B2 | 3/2008 | Vaughan et al. | |
| 7,992,422 B2* | 8/2011 | Leddy et al. | 73/23.3 |
| 8,087,283 B2* | 1/2012 | Wang et al. | 73/23.4 |
| 2003/0023181 A1* | 1/2003 | Mault | 600/532 |
| 2003/0065273 A1* | 4/2003 | Mault et al. | 600/531 |
| 2003/0109794 A1 | 6/2003 | Phillips | |
| 2003/0109795 A1* | 6/2003 | Webber | 600/543 |
| 2003/0208133 A1* | 11/2003 | Mault | 600/532 |
| 2004/0127808 A1* | 7/2004 | Vaughan et al. | 600/532 |
| 2004/0133116 A1 | 7/2004 | Abraham-Fuchs et al. | |
| 2005/0085740 A1 | 4/2005 | Davis et al. | |
| 2005/0150778 A1 | 7/2005 | Lewis et al. | |
| 2006/0222568 A1* | 10/2006 | Wang et al. | 422/70 |
| 2008/0148815 A1* | 6/2008 | Lucas et al. | 73/23.41 |
| 2008/0275355 A1* | 11/2008 | Namjou-Khaless et al. | 600/532 |
| 2009/0054799 A1* | 2/2009 | Vrtis et al. | 600/532 |
| 2009/0308136 A1 | 12/2009 | Wang et al. | |
| 2009/0326338 A1* | 12/2009 | Kobayashi et al. | 600/300 |
| 2010/0081955 A1* | 4/2010 | Wood et al. | 600/532 |
| 2010/0137733 A1* | 6/2010 | Wang et al. | 600/532 |
| 2010/0168599 A1* | 7/2010 | Esposito et al. | 600/532 |
| 2011/0001044 A1* | 1/2011 | Chou | 250/282 |
| 2011/0005300 A1* | 1/2011 | Wang et al. | 73/23.4 |
| 2011/0023581 A1* | 2/2011 | Chou et al. | 73/23.42 |
| 2011/0066060 A1* | 3/2011 | von Bahr et al. | 600/532 |
| 2011/0259081 A1* | 10/2011 | Chou et al. | 73/23.42 |
| 2012/0090378 A1* | 4/2012 | Wang | A61B 5/082 73/23.42 |

FOREIGN PATENT DOCUMENTS

| | | |
|---|---|---|
| JP | H02-046832 A | 2/1990 |
| JP | H06-047047 | 2/1994 |
| JP | H07-184488 A | 10/1995 |
| JP | 2005-512067 | 4/2005 |
| JP | 2005-530553 A | 10/2005 |
| JP | 2008-527353 | 7/2008 |
| JP | 2011-524536 | 9/2011 |
| WO | WO 2000/20852 A1 | 4/2000 |
| WO | WO 2000/32091 A2 | 6/2000 |
| WO | 2006/046588 A1 | 5/2006 |
| WO | WO-2006/076265 | 7/2006 |
| WO | 2008/091306 A2 | 7/2008 |
| WO | 2008/126519 A1 | 10/2008 |

OTHER PUBLICATIONS

ISA written opinion.*
Elevation of Exhaled Ethane Concentration in Asthma, Paolo Paredi, Sergei A. Kharitonov, and Peter J. Barnes; Am J Respir Crit Care Med vol. 162. pp. 1450-1454, 2000.*
Exhaled Ethane, a Marker of Lipid Peroxidation, Is Elevated in Chronic Obstructive Pulmonary Disease, Paolo Paredi, Sergei A. Kharitonov, David Leak, Simon Ward, David Cramer, and Peter J. Barnes; Am J Respir Crit Care Med vol. 162. pp. 369-373, 2000.*
Exhaled Pentane and Nitric Oxide Levels in Patients With Obstructive Sleep Apnea; Christopher O. Olopade; James A. Christon; Mohamed Zakkar; Chi-wei Hua; William I. Swedler; Peter A. Scheff; and Israel Rubinstein; CHEST 1997; 111:1500-04.*
An electronic nose in the discrimination of patients with asthma and controls; S Dragonieri, R Schot, BJA Merterns, S LeCessie, SA Gauw, A Spanevello, O Resta, EHBel, PJ Sterk; J Allergy Clin Immunol, Oct. 2007, 856-862.*
Office Action in Chinese Patent Application No. 200980155812.0 dated Jul. 31, 2013, 3 pages.
Chinese Office Action dated Mar. 5, 2013 for CN Patent Application No. 200980155812.0, with English Translation, 4 pages.
European Search Report dated Apr. 15, 2013 for EP Patent Application No. 09830923.0, 4 pages.
International Search Report for International PCT Application No. PCT/US2009/066103, dated Jan. 28, 2010, 2 pages.
International Preliminary Report on Patentability for International PCT Application No. PCT/US2009/066103, dated Jun. 7, 2011, 9 pages.
Office Action for Japanese Application No. 2011-538714 dated Feb. 12, 2014 with English summary, 4 pages.
Office Action for EPO Application No. 09830923.0 dated Feb. 26, 2014, 6 pages.
Cao et al., "Current Status of Methods and Techniques for Breath Analysis," Critical Reviews in Analytical Chemistry 37(1): 3-13 (2007).
Minakata et al., "Assessment of Obstructive Pulmonary Diseases (COPD or Asthma) by Exhaled Gas or Exhaled Breath Condensate," Pharma Medica 23(8): 23-27 (2005).
Yamagata et al., "Exhaled Gas Analysis," Respiration and Circulation 54(6): 591-598 (2006).
Decision to Grant a Patent for Japanese Patent Application No. 2011-538714 dated Oct. 27, 2015, 7 pages.
Minutes of the Oral Proceedings for European Patent Application No. 09830923.0 dated Apr. 20, 2018, 17 pages.
Notice of Allowance for Chinese Patent Application No. 201510181153.5 dated Nov. 14, 2018, 2 pages.
Notice of Reexamination for Chinese Patent Application No. 200980155812.0 dated Jun. 9, 2014, 8 pages.
Office Action for Chinese Patent Application No. 201510181153.5 dated Dec. 30, 2016, 16 pages.
Office Action for Chinese Patent Application No. 201510181153.5 dated May 14, 2018, 8 pages.
Office Action for Chinese Patent Application No. 201510181153.5 dated Oct. 24, 2017, 10 pages.
Office Action for India Patent Application No. 5071/DELNP/2011 dated May 28, 2018, 6 pages.
Office Action for Japanese Patent Application No. 2011-538714 dated Jan. 27, 2015, 12 pages.
Summons to Attend Oral Proceedings for European Patent Application No. 09830923.0 dated Jul. 27, 2017, 5 pages.
Beck-Ripp, J. et al., "Changes of exhaled nitric oxide during steroid treatment of childhood asthma", European Respiratory Journal, vol. 19, 2002, pp. 1015-1019.
Fend, Reinhard et al., "Prospects for Clinical Application of Electric-Nose Technology to Early Detection of Mycobacterium Tuberculosis in Culture and Sputum", Journal of Clinical Microbiology, vol. 44, No. 6, Jun. 2006, pp. 2039-2045.
Freeman, James A. et al., "Neural Networks—Algorithms, Applications, and Programming Techniques", Addison-Wesley Publishing Company, 1991, 414 pp. total.
Jones, Stuart L. et al., "The Predictive Value of Exhaled Nitric Oxide Measurement in Assessing Changes in Asthma Control", American Journal of Respiratory and Critical Care Medicine, vol. 164, 2001, pp. 738-743.
Phillips, Michael et al., "Prediction of lung cancer using volatile biomarkers in breath", Cancer Biomarkers, vol. 3, 2007, pp. 95-109.
Phillips, Michael et al., "Volatile biomarkers of pulmonary tuberculosis in the breath", Tuberculosis, vol. 87, 2007, pp. 44-52.
Zadeh, L. A., "Fuzzy Sets", Information and Control, vol. 8, 1965, pp. 338-353.
Zadeh, Lotfi A., "Outline of a New Approach to the Analysis of Complex Systems and Decision Processes", IEEE Transactions on Systems, Man, and Cybernetics, vol. SMC-3, No. 1, Jan. 1973, pp. 28-44.

* cited by examiner

VOC detection from ambient for possible TB bacteria contamination warning ambient air — 320 — Exhaled breath Gases of TB Culture — 330

Flow rate and volume control/measurement

VOCs detectors — 350 ambient air — 310

VOC detection from exhaled breath or from gases of TB culture
1. Assessment of TB infection
2. Management of TB medication
3. Drug resistance test of TB — 380

*FIG. 3*

Level of severity is determined by assessment of both impairment and risk. Assess impairment domain by patient's/caregiver's recall of previous 2-4 weeks and spirometry. Assign severity to the most severe category in which any feature occurs.

At present, there are inadequate data to correspond frequencies of exacerbations with different levels of asthma severity. In general, more frequent and intense exacerbations (e.g., requiring urgent, unscheduled care, hospitalization, or ICU admission) indicate greater underlying disease severity. For treatment purposes, patients who had >2 exacerbations requiring oral systemic corticosteroids in the past year may be considered the same as patients who have persistent asthma, even in the absence of impairment levels consistent with persistent asthma.

■ Classifying severity in patients after asthma becomes well controlled, by lowest level of treatment required to maintain control.*

| Lowest level of treatment required to maintain control | Classification of Asthma Severity | | | |
|---|---|---|---|---|
| | Intermittent | Persistent | | |
| | Step 1 | Mild | Moderate | Severe |
| | | Step 2 | Step 3 or 4 | Step 5 or 6 |

Key: EIB, exercise-induced bronchospasm; $FEV_1$, forced expiratory volume in 1 second; FVC, forced vital capacity; ICU, intensive care unit

*Notes:

For population-based evaluations, clinical research, or characterization of a patient's overall asthma severity after control is achieved. For clinical management, the focus is on monitoring the level of control, not the level of severity, once treatment is established.

*FIG. 9B*

BREATH ANALYSIS SYSTEMS AND METHODS FOR ASTHMA, TUBERCULOSIS AND LUNG CANCER DIAGNOSTICS AND DISEASE MANAGEMENT

CROSS-REFERENCE TO RELATED APPLICATIONS

This application claims priority to U.S. Provisional Patent Application No. 61/118,977, filed Dec. 1, 2008, the contents of which is hereby incorporated by reference in its entirety for all purposes.

FIELD OF THE INVENTION

The present invention provides systems and methods for low-cost, rapid and accurate diagnosis and monitoring of respiratory ailments such as infections and chronic illnesses and especially asthma, tuberculosis and lung cancer using gas sensor technology.

BACKGROUND OF THE INVENTION

Clinical studies on human breath analysis have discovered that certain trace gases from human breath are correlated to certain diseases, especially for lung-related diseases such as asthma, tuberculosis (TB), and lung cancer (see, M. Philips, et al., *Cancer Biomarkers,* 3:95-109 (2007); M. Philips, et al., *Tuberculosis,* 87:44-52 (2007)). In other applications, gas analysis can be used to determine the presence of dangerous substances or fugitive gases, which are incompatible with human presence, such as methane, carbon monoxide or carbon dioxide.

Current gas analytical systems still rely heavily on large and expensive laboratory instruments, such as gas chromatography (GC) and mass spectrometry (MS). Most of these instruments (mass spectrometers in particular) have operational characteristics that prevent significant reductions in their size, meaning that current gas analysis systems are large, expensive devices and are difficult to operate (e.g., laboratory size GC/MS).

In addition to being expensive, the large size of current gas analysis devices makes widespread use of these instruments impossible. Point of care analysis would be highly beneficial, however, no systems are currently available.

Asthma is a chronic lung disease characterized by recurrent episodes of coughing, wheezing, chest tightness and respiratory discomfort. Pulmonary inflammation contributes to the bronchoconstriction that can precipitate an asthma attack, and the progression of this chronic disease. It is estimated that over 20 million people in the United States have asthma. The National Heart Lung and Blood Institute notes that asthma accounts for $16.1 billion in direct and indirect healthcare costs annually.

TB kills roughly two million people every year and is one of the world's best-studied killers. TB diagnostics have remained unchanged for decades, despite their acknowledged poor performance. Current diagnostic methods include sputum smear microscopy, culture, and chest X-rays. However, these methods either have poor sensitivity (45-60% for smear microscopy), poor specificity (~66% for X-ray), or are too slow (3-6 weeks for culture).

Recent studies show TB tests based on patients' exhaled VOCs and gases of cultured microbacteria have very high sensitivity and specificity using a GC/MS instruments (see, Michael Phillips, et al., *Tuberculosis* 87:44-52 (2007); Reinhard Fend, *J. Clin. Microb., p.* 2039-2045 (June 2006)). But this method requires very sophisticated setup and it is not practical to be used in the field.

Lung cancer is a disease of uncontrolled cell growth in tissues of the lung. The majority of primary lung cancers are carcinomas of the lung, derived from epithelial cells. Lung cancer, the most common cause of cancer-related death in men and also the most common in women, is responsible for 1.3 million deaths worldwide annually. The main types of lung cancer are small cell lung carcinoma (SCLC) and non-small cell lung carcinoma (NSCLC). This distinction is important, because the treatment varies; non-small cell lung carcinoma (NSCLC) is sometimes treated with surgery, while small cell lung carcinoma (SCLC) usually responds better to chemotherapy and radiation.

System and methods are needed which enable human breath analysis for the detection and diagnosis of asthma, tuberculosis and lung cancer. A device is needed for breath analysis and ambient air monitoring that is easy to use, and has high sensitivity and specificity. The present invention satisfies these and other needs.

SUMMARY OF THE INVENTION

The present invention provides systems and methods for enabling human breath analysis for the detection, diagnosis and monitoring of respiratory ailments, lung infections and chronic illnesses. Methods for drug efficacy testing are also disclosed.

In one embodiment, the present invention provides a method for detecting whether a subject has asthma or monitoring a subject with asthma, comprising:
contacting breath from the subject with an apparatus, the apparatus having a gas chromatograph, wherein the gas chromatograph is fluidly coupled to a detector array to produce a signal; and
analyzing the signal from the detector array to determine whether the subject has asthma.

In a preferred embodiment, the apparatus further comprises a preconcentrator upstream of the gas chromatograph.

Advantageously, the systems and methods increase the specificity, sensitivity and dynamic range of monitoring the grade and severity of asthma over prior art techniques by detecting VOCs, and/or NO, and/or breath flow rate.

In one aspect, the systems and methods can monitor VOCs for a patient with mild or no asthma. The ambient air is monitored and can be saved as a background signal for reference. In one aspect, the ambient air is filtered before inhaled by patient. In an alternative embodiment, the saved background signal is then filtered or subtracted from the signal detected from exhaled breath.

In certain instances, decisions regarding medication can be managed by monitoring VOCs, NO, and flow rate such as prior to, during and/or after medication treatment. Moreover, the systems and methods disclosed herein provide an early warning of environmental contaminates for asthma patients thereby alerting patients to avoid certain environmental VOCs.

The methods and systems disclosed herein can be implemented in various formats and platforms such as portable, handheld or laboratory instruments. The apparatus can be included or integrated into a gas analyzer, such as GC/MS, GC/FID, GC/optical laser detectors, GC/nano particle sensor, GC/QCM and eNose devices.

In another embodiment, the present invention provides systems and methods for the detection of TB which are accurate, rapid, and portable such as a point-of-care service which are surprisingly affordable.

As such, the present invention provides a method for detecting whether a subject has tuberculosis or monitoring a tuberculosis subject, comprising:

contacting headspace from a subject's sample or the breath of a subject with an apparatus, the apparatus having a gas chromatograph, wherein the gas chromatograph is fluidly coupled to a detector array to produce a signal; and analyzing the signal from the detector array to determine whether the subject has tuberculosis.

In a preferred embodiment, the apparatus further comprises a preconcentrator upstream of the gas chromatograph.

Advantageously, the systems and methods disclosed herein are highly sensitivity, with high specificity for TB tests based on a patient's exhaled VOCs and/or gases of cultured TB bacteria. The test and analysis is rapid and can be done within minutes.

In certain aspects, the systems and methods are portable and inexpensively detect VOCs of TB patients before, during and after medication to effectively manage and control a TB patient's medication treatment. In an alternative aspect, the systems and methods monitor VOCs of a TB culture or a patient before, during and/or after various drug treatments to identify the most effective drug for drug-resistant TB bacteria.

In addition, the systems and methods disclosed herein monitor volatile organic compounds (VOCs) of headspace gases from a subject's sputum or a sputum culture to diagnose whether patient has TB.

In certain other aspects, the present methods and systems use a subject's breath, sputum or sputum culture to detect a TB infection. In certain aspects, headspace sampling from mycobacterium cultures can be used to detect drug resistance bacteria during treatment. Medical professionals can detect VOCs of TB patients during the medication to effectively manage and control the TB patients' medication treatment. Further, the methods and systems herein allow the monitoring of VOCs from cultures for drug resistance testing.

In still yet another embodiment, the present invention provides a method for detecting whether a subject has lung cancer or monitoring a subject with lung cancer, comprising:

contacting breath from the subject with an apparatus, the apparatus having a gas chromatograph, wherein the gas chromatograph is fluidly coupled to a detector array to produce a signal; and analyzing the signal from the detector array to determine whether the subject has lung cancer.

In a preferred embodiment, the apparatus further comprises a preconcentrator upstream of the gas chromatograph.

Other objects, features, and advantages of the present invention will be apparent to one of skill in the art from the following detailed description and figures.

BRIEF DESCRIPTION OF THE DRAWINGS

FIG. 3 illustrates one embodiment of the invention for the detection and monitoring of TB.

FIGS. 9A-B together illustrates one embodiment of a classification scheme for asthma.

DETAILED DESCRIPTION OF THE INVENTION

I. Introduction

The present invention provides systems and methods useful for low-cost, rapid and accurate diagnosis and monitoring of respiratory ailments such as infections and chronic illnesses. Using gas analysis system technology, the systems and methods disclosed herein can detect chemical and biological marker gases to provide clinical data to healthcare professionals and/or patients for low-cost, rapid and accurate diagnosis of asthma, TB and lung cancer. Methods for drug efficacy testing are also disclosed.

II. Embodiments

A. Asthma

In one aspect, the present systems and methods provide rapid and accurate diagnoses and monitoring of asthma. Asthma is generally considered a chronic inflammatory disease that affects the airways of children and adults, which causes shortness of breath, a tightening in the chest, and is accompanied by coughing, wheezing and respiratory discomfort. Symptoms of asthma can vary from person to person. Asthma symptoms further include blockage of the flow of air to a subject. In other words, the inhaled and exhaled breath of the subject is less than in a normal individual. Typically this happens because the airway lining becomes inflamed, irritated, and/or swollen. Mucous secretions can also block the airways, and the more inflamed the airway, the more sensitive the airway becomes perpetuating more symptoms. The inflammation can also cause the muscles to tighten which is referred to as bronchospasm, which makes it increasingly difficult to breathe.

Figure 1A:
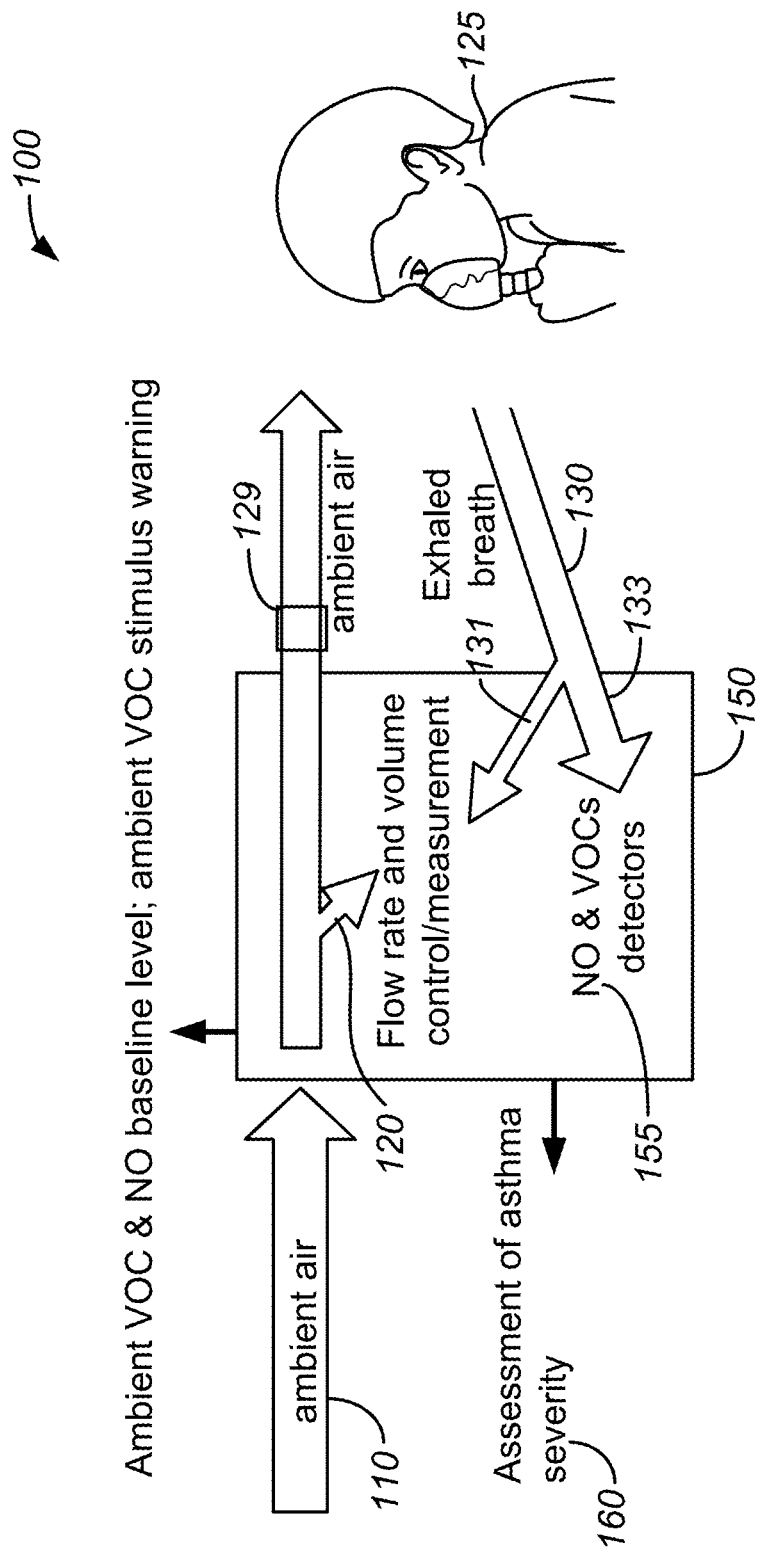
FIG. 1A-C illustrate one embodiment of the invention for the detection and monitoring of asthma; Panel B illustrates a mouth and lung wash and Panel C illustrates a mouth and lung wash.

FIG. 1A illustrates one embodiment of the present invention wherein systems and methods 100 for detecting whether a subject has asthma or monitoring a subject with asthma is shown. The method includes contacting ambient air 110 from the inhaled breath from a subject 125 with an apparatus. The flow rate and volume 120 of the inhaled breath are optionally measured or/and controlled, and ambient volatile organic compounds (VOCs) and nitric oxide (NO) are measured as baseline level (e.g., for reference). In certain aspects, the VOCs from the background or ambient air can be filtered out by a filter (e.g., inline) and thereby eliminated 129. The filtered inhaled breath then enters the lung of the subject 125. The exhaled breath 130 then enters the apparatus. Optionally, there can be a preconcentrator for the exhaled breath 133 (e.g., inline). One example of the apparatus includes a preconcentrator module (for either inhaled breath, exhaled breath or both), a gas chromatograph module and a detector array module 150. The detector array module 150 produces a signal indicative of various biomarkers 155 such as VOCs and NO. The signal is analyzed to determine whether the subject has asthma 160 and/or its severity and grade.

In certain aspects, the portable gas analyzer optionally comprises a module that regulates the flow of exhaled breath. The exhaled breath can be assisted or regulated to a desired flow rate. The module or flow meter 131 (e.g., inline) controls the rate of air flow directly of the exhaled breath 130. Although the flow rate of the analyte-containing gas through the sensor chamber can vary, the rate can be increased or decreased by the module or flow meter. In one embodiment, a flow rate of about 200 mL/min to about 1000 mL/min is used. In other instances, the flow rate is about 300 mL/min to about 750 mL/min. In still other instances, the flow rate is about 400 mL/min to about 650 mL/min. In still yet other instance, the flow rate may be fixed at certain rates such as, for example, 600 mL/min, 1000 mL/min, 3000 mL/min, or 6000 mL/min, but actual measurements are not limited by these flow rates.

Figure 1B:
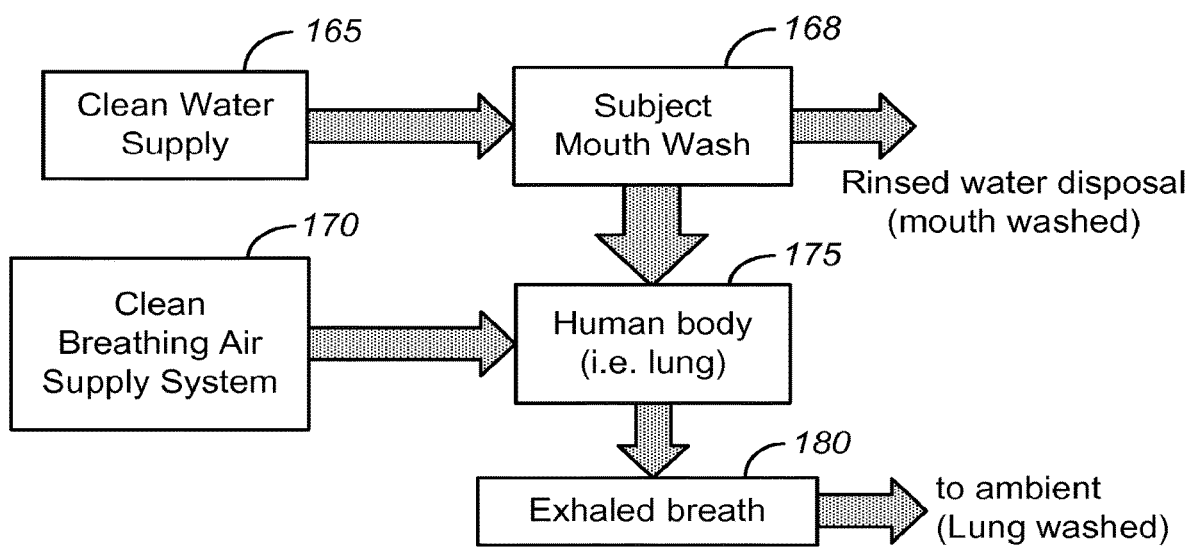
Figure 1C:
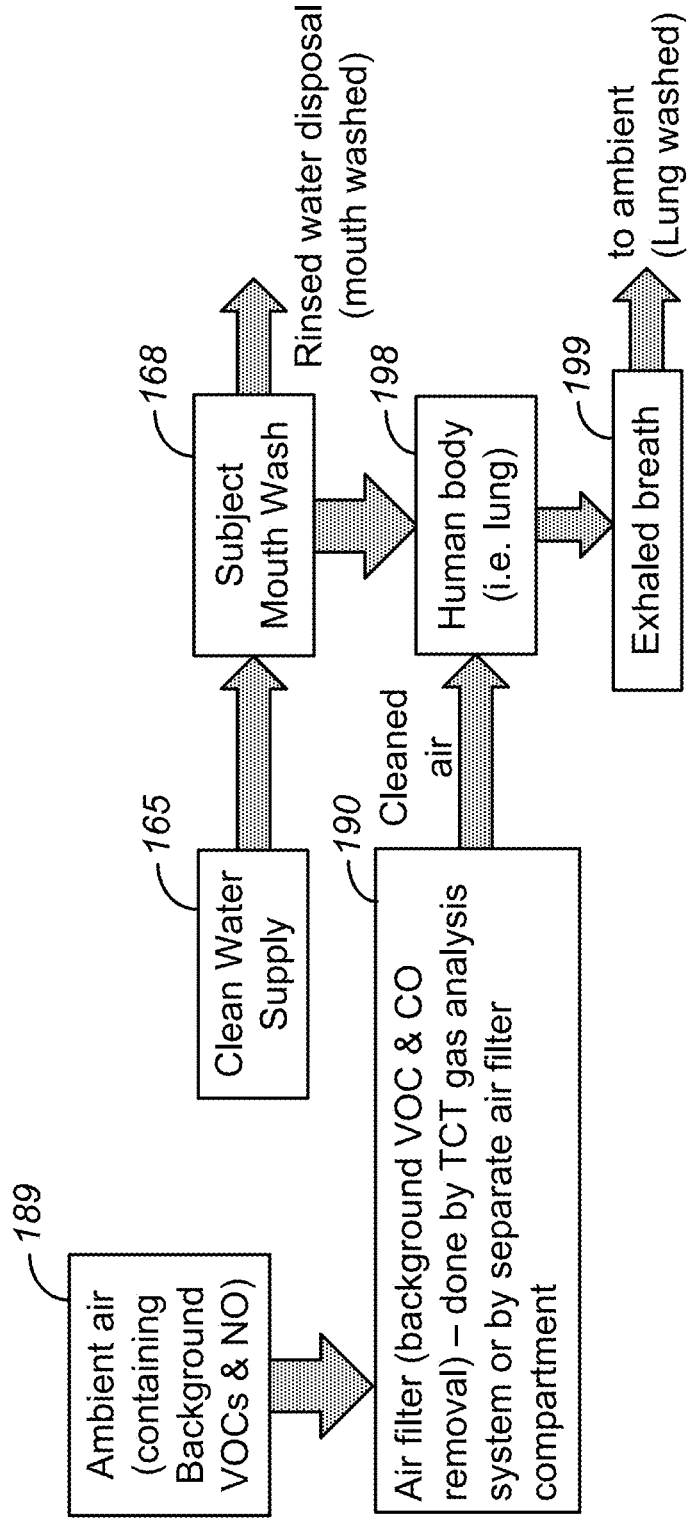

In certain instances, before repeat measurements are taken, the methods optionally include a "lung washout," protocol wherein several deep breaths are taken with pure air by the individual and not measured. In addition, a mouth wash protocol may optionally be included prior the actual measurement. For example, turning to FIG. 1B, a clean water supply 165 is given to the subject to rinse and wash their mouth 168, and thereafter discarded. In an analogous way, a clean air supply system 170 is given to the subject 175 to clean the ambient air and is then exhaled 180. In an alternative embodiment, as is shown in FIG. 1C, ambient air containing VOCs and NO 189 is filtered to remove all ambient VOCs and NO 190. In this manner, clean air is passed to the human lung 198 devoid of VOCs and NO. The breath is exhaled 199 and the lung is washed.

In certain instances, the exhaled breath rate is increased by the module 131 (FIG. 1A) with a fan or pump, or by diluting it with additional air, such as compressed air. In one aspect, the analyte in the gas phase can be further diluted by mixing it with another gas, such as air. In addition, humidity can be introduced into the gas sample by bubbling air (or an inert gas) through water at a given temperature, and then mixing it with the gas containing the analyte vapor. The rate of the exhaled air can be reduced using the module to restrict air flow.

In certain aspects, the methods herein employ a portable gas analysis system (PGAS) with a small form factor such as disclosed in U.S. patent application Ser. No. 12/140,822 filed Jun. 17, 2008 and entitled "Handheld Breath Analysis Microsystems for Rapid Disease Classification, Disease Diagnostics and Health Monitoring," which is incorporated herein by reference. In certain aspects, the breath analysis and ambient air monitoring can be done routinely by physician and patients. Furthermore, the methods and systems disclosed herein can be applied to bench-top or central-lab instruments, such as, for example, a GC/MS.

In certain embodiments, the breath of the subject contains markers or biomarkers suitable for the detection, diagnosis and monitoring of for example, asthma. In certain aspects, the biomarker detected by the methods and systems is a volatile organic compound (VOC) or a plurality of such compounds (VOCs). In certain aspects, the VOC is a member selected from the group of 4-methyloctane, 2,4-dimethylheptane, isopropanol, toluene, isoprene, alkane, acetic acid, acetone, 2,6,11-trimethyl dodecane, 3,7-dimethyl undecane, 2,3-dimethyl heptane or a combination thereof. In certain aspects, the breath gas or marker is nitric oxide. Advantageously, the methods of the present invention enable detecting both NO and VOCs from exhaled breath with increased specificity and greater dynamic range compared to prior art methods.

In certain other instances, exhaled NO concentration measurements correlate with asthma control during treatment (see, for example, Jones S L, Kittelson J, Cowan J O et al., *Am J Respir Crit Care Med.*; 164:738-743 (2001); Beck-Ripp J, Griese M, Arenz S, et al., *Eur. Respir. J.*, 19:1015-1019 (2002)). In certain instances, NO concentration levels can be an overall marker of airway inflammation. As such, in certain embodiments, the NO concentration level in conjunction with VOCs can be used to detect, diagnose and monitor asthma.

In certain aspects, ambient air is monitored for VOCs and saved as a baseline level for reference. The inhaled air is filtered from the ambient VOCs before entering the patient's lung. In other words, by filtering the ambient VOCs, the subject inhales VOC-free air. The inhaled breath is also measured for flow rate and volume. The exhaled breath is collected for NO and VOCs detection together with reference of flow rate and volume for asthma assessment.

In a preferred aspect, the grade and severity of asthma is determined. A VOC concentration or a plurality of VOCs is used to characterize or diagnose asthma as intermittent, mild, moderate or asthma. In another embodiment, NO concentration level is used to characterize asthma as severe asthma. The grade of asthma is usually categorized as being intermittent, mild, moderate, severe or combinations of the foregoing such as mild to moderate or moderate to severe. The systems and methods of the present invention give high specificity and high sensitivity for the diagnosis of asthma. Advantageously, the methods and systems of the present invention enhance dynamic range are very accurate and thus can differentiate the grade and severity of asthma (e.g., mild from severe).

In certain preferred aspects, NO concentration levels and VOCs identity and amounts of the exhaled human breath are correlated to grade and severity of asthma.

As used herein, the term "sensitivity" refers to the probability that a diagnostic method or system of the present invention gives a positive result when the sample is positive, e.g., a subject has the disease (e.g., asthma). Sensitivity is calculated as the number of true positive results divided by the sum of the true positives and false negatives. Sensitivity essentially is a measure of how well a method or system of the present invention correctly identifies those with the disease (e.g., asthma) from those without the disease. In preferred embodiments, the sensitivity of classifying the disease (e.g., asthma) is at least about 90% such as about 91%, 92%, 93%, 94%, 95%, 96%, 97%, 98%, or 99% using the systems and methods herein.

The term "specificity" refers to the probability that a diagnostic method or system, of the present invention gives a negative result when the sample is not positive, e.g., not having the disease (e.g., asthma). Specificity is calculated as the number of true negative results divided by the sum of the true negatives and false positives. Specificity essentially is a measure of how well a method or system of the present invention excludes those who do not have the disease (e.g., asthma) from those who have the disease. In preferred embodiments, the specificity of classifying is at least about 90% such as about 91%, 92%, 93%, 94%, 95%, 96%, 97%, 98%, or 99% using the systems and methods herein.

In certain preferred aspects, the methods and systems herein include the flow rate and volume measurements for the subject. The apparatus includes a spirometer to measure the flow rate and/or volume of the inhaled, exhaled or both the inhaled and exhaled breath. In certain instances, the patient breathes in methacholine which induces airway narrowing. This procedure can give additional data for the calculation of the grade of asthma. Those of skill in the art will know of other methods useful in the present invention.

In certain aspects, the efficacy of a therapeutic can be monitored with periodic breath samples using the methods of the present invention. For example, if an inhaled corticosteroids is used or a bronchodilator is used, the treatment can be assessed with the methods of the present invention.

In certain aspects, the methods herein include measuring the flow of breath such as inhaled, exhaled or both, preferably using a spirometer. The spirometer module is preferably integral to the apparatus. In certain instances, the volume and speed of airflow from the breath is measured. Subjects can use the apparatus optionally wearing a nose clip, breathing in and out through a disposable mouthpiece. Breath is then sampled at approximately 2.0 liters/min for about 2-5 minutes and drawn through a preconcentrator to capture the VOCs. A sample of ambient room air is collected in a similar fashion onto another preconcentrator. In certain aspects, the subject is on a ventilator such as in a hospital setting, and so the apparatus disclosed herein is in fluid communication with the lung of the subject.

In certain aspects, the breath of the subject is from a bag configured to collect breath from the subject (see, for example, U.S. Pat. No. 5,465,728 or 6,723,056). The breath can be concentrated using the preconcentrator module of the apparatus. In certain aspects, the preconcentrator module comprises sorbent or material having affinity for the VOCs of interest. The preconcentrator module is heated to desorb the VOC in order for further analysis.

Advantageously, with certain analytes, such as high vapor pressure analytes, the analyte is concentrated on an absorbent. The preconcentrator can be used to increase the concentration of analytes in the test sample. Preconcentrators are traps composed of an adsorbent material. In use, an adsorbent material attracts molecules from the gas sample that are concentrated on the surface of the adsorbent. Subsequently, the sample is "desorbed" and analyzed. Suitable preconcentrator materials include, but are not limited to, a polymeric adsorbent material, unsilanized glass wool, Teflon or porus glass fiber, and the like. The adsorbent material is packed in a tube, such as a steel tube.

In still other aspects, the present methods provide monitoring of ambient air for an environmental warning. By monitoring the ambient air, such as for viruses, allergens, fumes, and smoke, an asthma patient can be put on alert regarding the presence of such harmful elements. Based upon the asthma-causing factors for an individual patient, the methods herein can be programmed to lock-on to certain gases by, for example, pattern recognition. In one aspect, the ambient air is stored as a background signal that can be subtracted from the subject's breath.

Figure 2A:
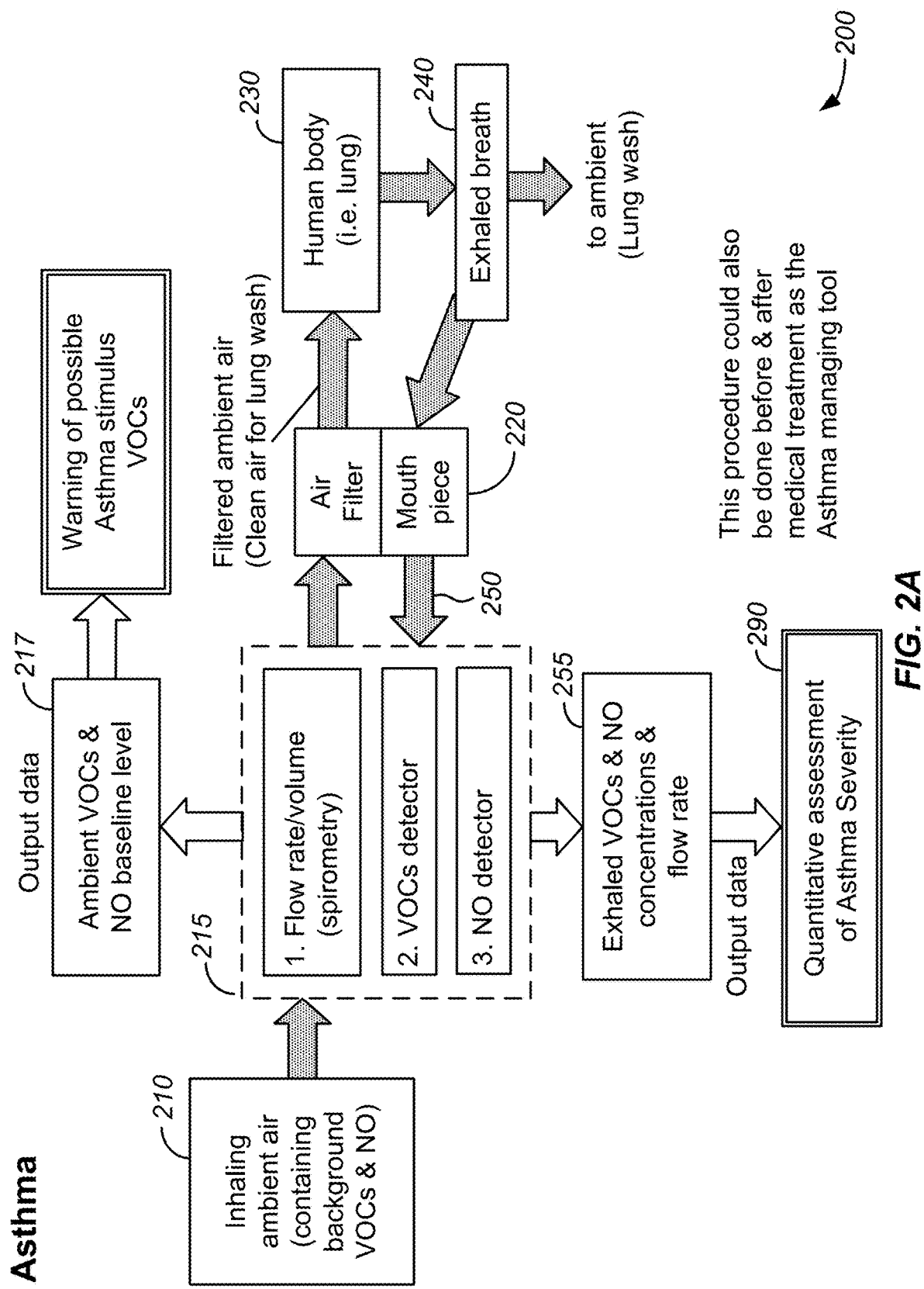
FIG. 2A-B illustrate embodiments of the invention for the detection and monitoring of asthma; Panel B illustrates one embodiment of the invention for the detection and monitoring of asthma.
Figure 2B:
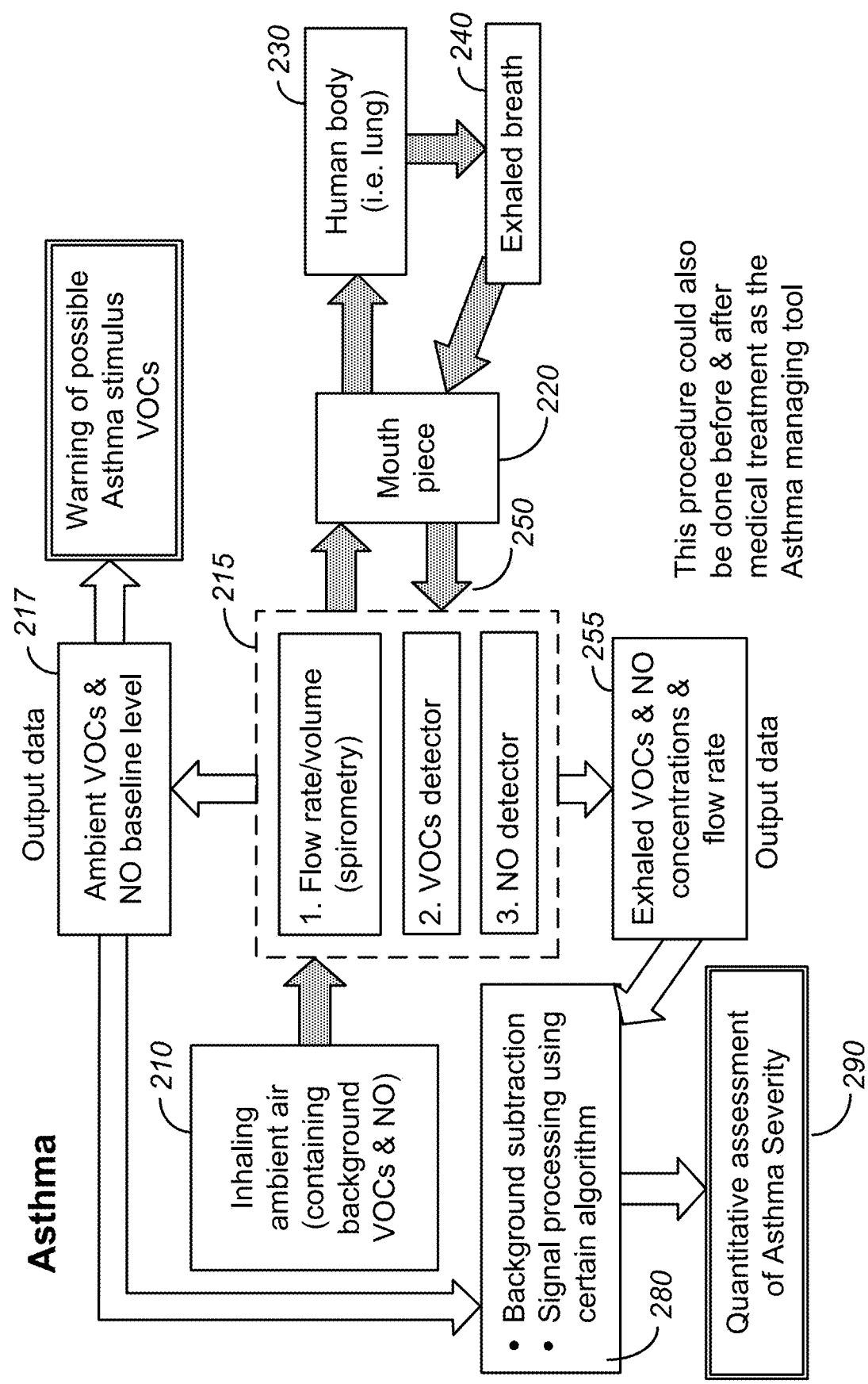

Turning now to FIG. 2A, as shown therein, the present methods provide monitoring of ambient air 200 for an environmental warning alerting the patient from entering an environment. The inhaling ambient air 210 contains background VOCs and NO gas. The apparatus contains an analyzer 215 having a spirometer (1), and a detector array module comprising a VOC detector (2), a NO detector (3) which outputs an ambient air VOC and NO baseline level 217. If the levels are too high i.e., above a threshold level, a warning such as a red light or sound is made to alert the user of the inhospitable environment. By monitoring the ambient air, such as for viruses, allergens, fume, smoke, dust and the like for early environmental containments, the systems and methods warn asthma patients. Based on the asthma causing factors of an individual patient, the device can be programmed to lock-on certain gases by pattern recognition algorithms. The systems and methods are in fact in certain instances, a personalized environmental detection device for specific allergens for early warning to asthma patients. In certain aspects, the present systems and methods have a mouth piece and filter (e.g., disposable) 220 for ease of operation. In one embodiment, the VOCs of ambient air are physically filtered out before entering the lung. The lungs of the individual 230 provides the means to take in air and exhale air 240 through the system. The exhaled air 240 travels 250 to the analyzer 215. The output data 255 can be assessed for exhaled VOCs, and NO concentration as well as flow rate. As is shown in FIG. 2B, in an alternative embodiment, background subtraction 280 can then take place using signal processing and data manipulations using certain algorithms. A quantitative assessment of asthma severity 290 can then be given.

In certain instances, the detector array is removable, replaceable and/or disposable. The detector array can be inserted and removed in a "plug-in-play" mode for particular enhancements and functionality.

The methods disclosed herein include aspects wherein regular monitoring of a subject's status is undertaken which is helpful to the healthcare professional or patient for tracking the subject's progress. In certain instances, the breath analysis described herein can provide the root cause of the bronchi constriction by measuring the VOCs from the subject's breath. In particular embodiments, portable gas analysis systems are used to monitor the efficacy of medication and therapy. Further, the medication therapy can be tailored to an individual patient (personalized device) through this active monitoring by using a home-based device.

In one aspect, medical professionals detect both NO and VOCs of asthma patients before and after medication. This can be an effective tool to manage and/or control the patient's medication treatment. In one aspect, if the patient continues to have high NO levels after treatment, this is due to inflammation in another area of the body and not asthma. However, detecting additional VOCs can indicate the healing of asthma.

In one aspect, a patient's NO level and VOC levels are measured in various time intervals. For example, it is possible to measure a patient's breath and monitor or calculate NO level and VOC concentration levels at T1 (time 1). At T2 (time 2), some time after T1, a patient's NO level and VOC concentration levels are again measured. The difference between T1 and T2 can be 1 week, 2 weeks, 3 weeks, 1 month, 2 months, 3 months, 4 months, 5 months, 6 months, 7 months, 8 months, 9 months, 10 months, 11 months, 1 year, 2 years, and the like.

B. Tuberculosis (TB)

In still other embodiments, the present invention provides methods and systems for the detection of whether a subject has tuberculosis or monitoring a tuberculosis subject. Turning now to FIG. 3, as shown therein, the present methods provide monitoring of ambient air 310 for an environmental warning altering the patient from entering an environment. The exhaled breath 320 or headspace gases from a subject's sputum (e.g., mucus, phlegm, saliva, etc., not shown), or a sputum culture 330 contains VOCs 350 which are contacted with the gas analyzer to produce a signal. The signal can be used to diagnose whether a patient has TB 380 or whether the TB infection is drug resistant, management of TB, etc. In certain instance, before repeat measurements, the methods include a "lung washout," protocol wherein several deep breaths are taken and not measured.

In certain preferred aspects, the methods and systems disclosed herein are important to ensure patients are given effective treatment in order to prevent drug-resistant TB. Currently, a relative rapid culture test (e.g., 9-15 days) by MGIT systems provides 95-97% accuracy (i.e., the degree of closeness to the accepted value) by measuring the $O_2$ consumption. However, the test is still very slow compared to the present method. The test requires trained technicians, proper bacteriological laboratory facilities and is relatively expensive compared to the simple rapid methodology of the present invention.

In certain aspects, the methods and systems of the present invention monitor VOCs of a patient's breath or headspace gases from the patient's sputum culture before, during and/or after therapeutic treatment or drug treatment on the sputum or sputum's culture to identify the most efficacious medication for TB bacteria for the patient. Also, active monitoring can decide the best timing to stop the medication.

In the illustrated embodiments, the elements are made replaceable by mounting them onto a substrate of the apparatus using sockets: a filter and valve assembly is mounted to the substrate by a socket, a preconcentrator is mounted to the substrate by a socket, a gas chromatograph is mounted to the substrate by a socket, a detector array is mounted to the substrate by a socket, and a pump is mounted to the substrate by a socket.

The substrate can be any kind of substrate that provides the required physical support and communication connections for the elements of device. In one embodiment, the substrate can be a printed circuit board (PCB) of the single-layer variety with conductive traces on its surface, but in other embodiments it can be a PCB of the multi-layer variety with conductive traces in the interior of the circuit board. In other embodiments, for example an embodiment where device is built as a monolithic system on a single die, the substrate can be chip or wafer made of silicon or some other semiconductor. In still other embodiments, the substrate can also be a chip or wafer in which optical waveguides can be formed to support optical communication between the components of device.

Figure 4A:
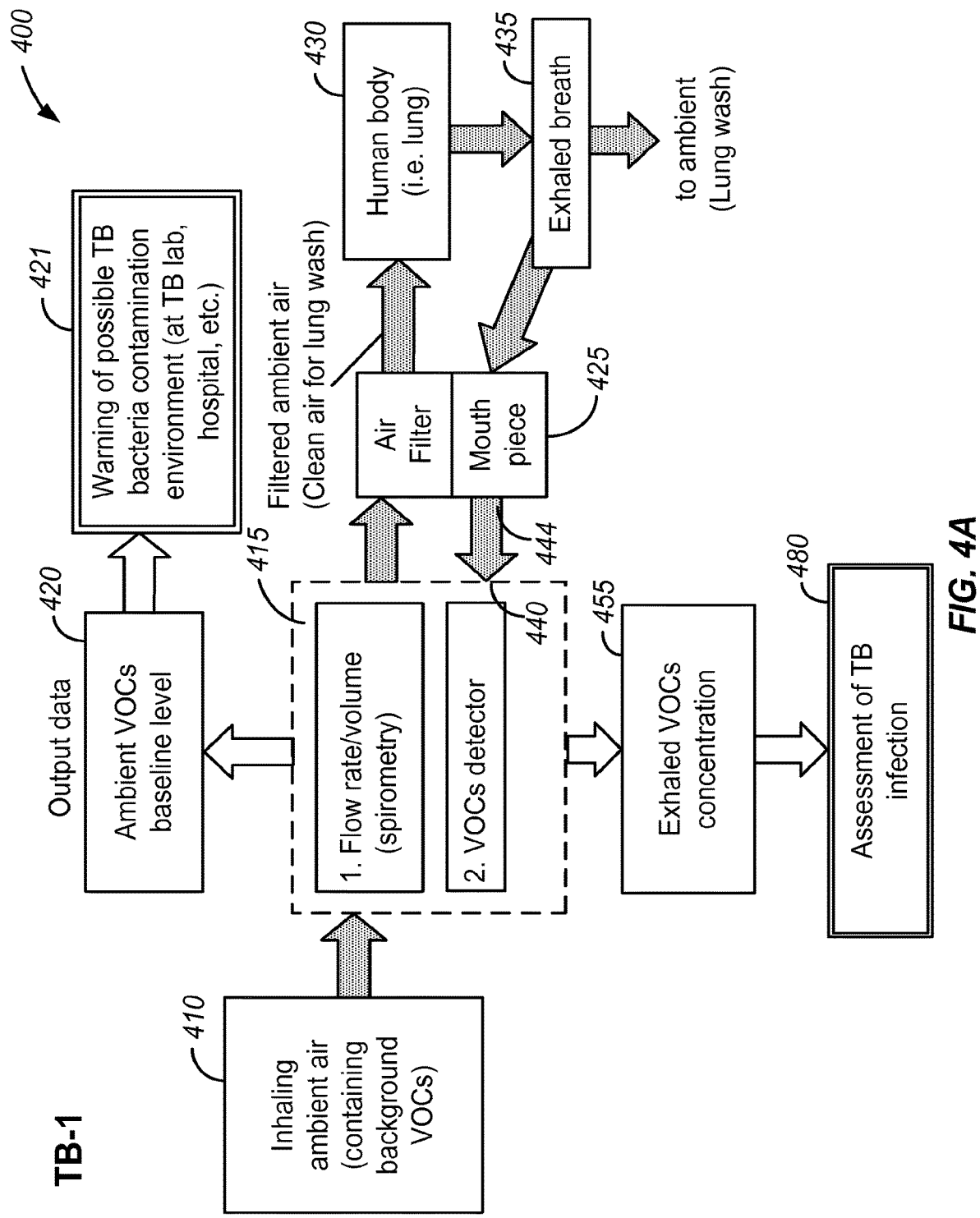
FIG. 4A-B illustrate embodiments of the invention for the detection and monitoring of TB; Panel B illustrates an embodiment of the invention for the detection and monitoring of TB.
Figure 4B:
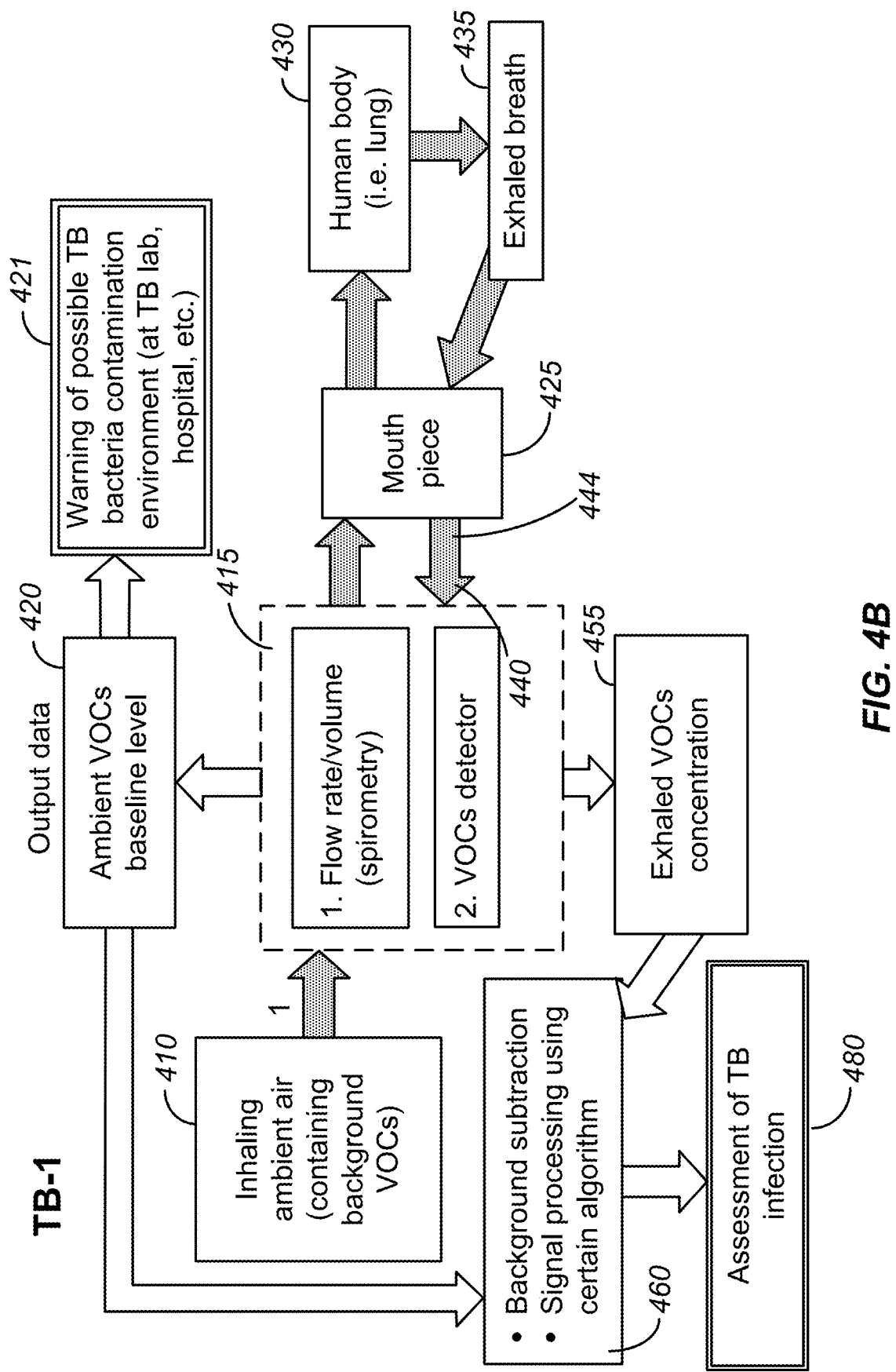

As shown in FIG. 4A, in one embodiment 400 of the methods disclosed herein, the subject inhales ambient air 410 containing background VOCs which are passed through the analyzer 415 having a spirometer (1) and a VOC detector array (2). The output data 420 has ambient VOCs baseline level measured against a threshold. If the output data exceeds the threshold, a warning 421 is communicated. In certain instances, the present systems and methods have a disposable mouth piece and filter 425 for ease of operation. The VOCs of ambient air are filtered before entering the lung 430. The lungs of the individual 430 provide the means to inhale air and exhale air 435 through the system. The exhaled air travels to the analyzer 415. In an optional embodiment, the apparatus contains a preconcentrator 440 (e.g., in-line) and/or a flow meter module 444 (e.g., in-line). The exhaled breath can be concentrated in order to concentrate VOCs. In addition, the flow meter module can regulate the flow of exhaled breath. The exhaled breath can be assisted or regulated to a desired flow rate. The module or flow meter 444 controls the rate of air flow directly by either restricting air flow or increasing air flow as explain previously. The output data 455 can be assessed for exhaled VOCs. In an alternative embodiment, background subtraction 460 (See, FIG. 4B) can then take place using signal processing and data manipulations. Advantageously, a quantitative assessment of a TB infection 480 can then be given.

Figure 5A:
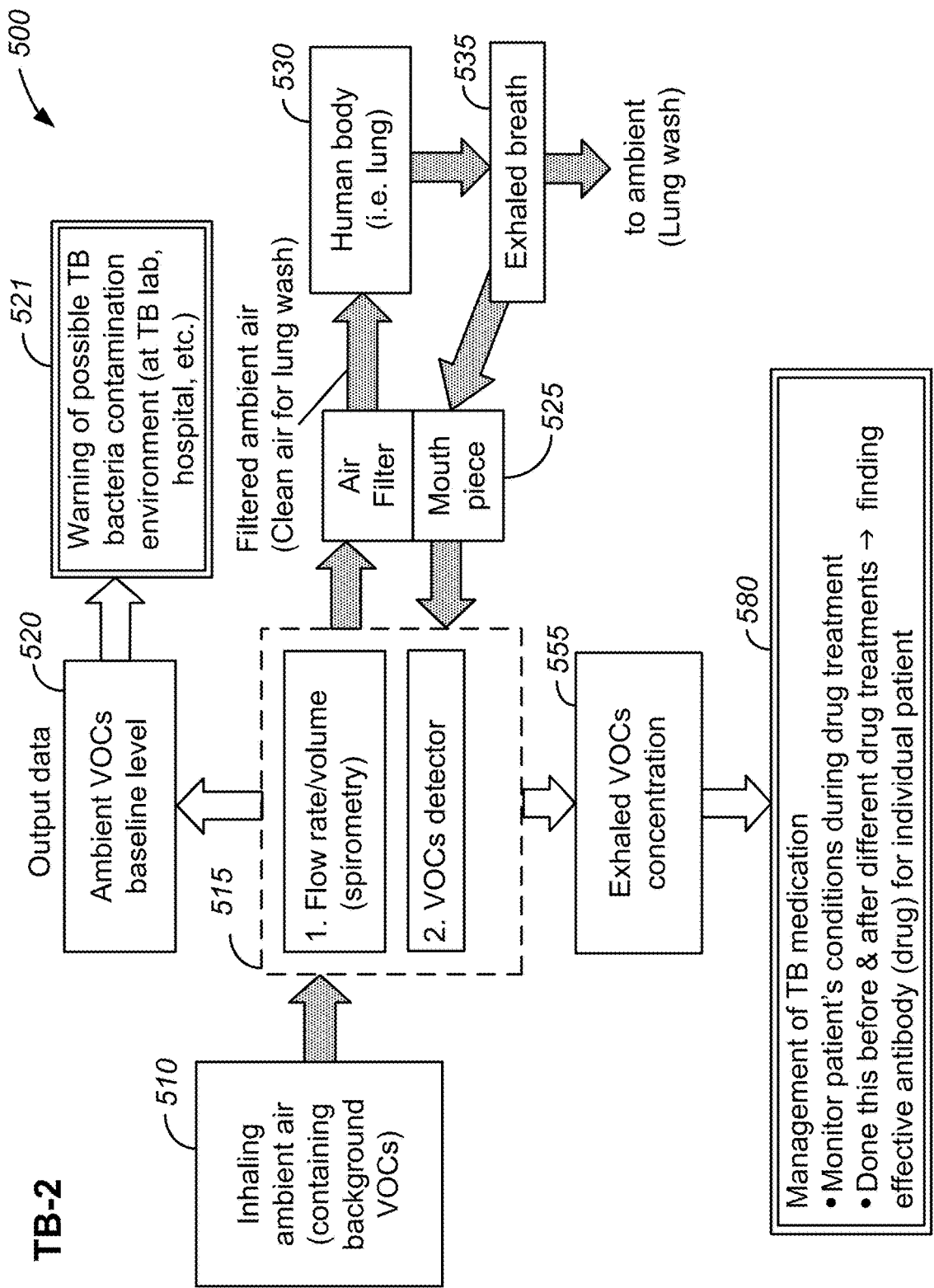
FIG. 5A-B illustrate embodiments of the invention for the detection and monitoring of TB; Panel B illustrates an embodiment of the invention for the detection and monitoring of TB.
Figure 5B:
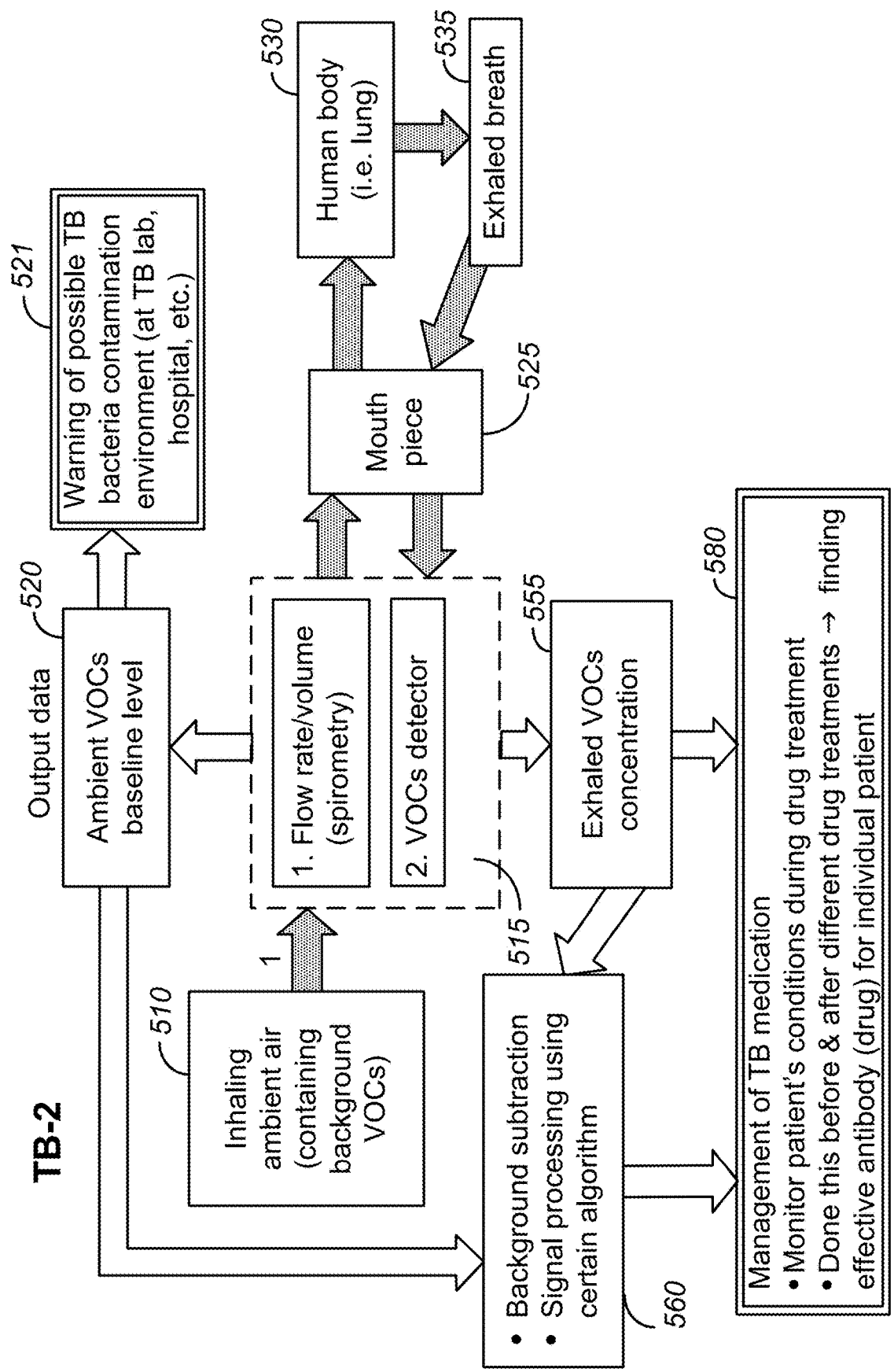

In another embodiment 500 shown in FIG. 5A, the subject inhales ambient air 510 containing background VOCs which are passed through the analyzer 515 having a spirometer (1) and a VOC detector (2). Again, the output data 520 has ambient VOCs baseline level measured against a threshold. If the output data exceeds the threshold, a warning 521 is communicated. In certain instances, the present systems and methods have a mouthpiece and filter (e.g., disposable) 525 for ease of operation. The VOCs of ambient air are filtered before entering the lung. The lungs of the individual 530 provide the means to inhale air and exhale air 535 through the system. The exhaled air travels to the analyzer 515. The output data 555 can be assessed for exhaled VOCs. In an alternative embodiment, background subtraction 560 (see, FIG. 5B) can then take place using signal processing and data manipulations using certain algorithms. Advantageously, management of TB medication 580 can be accomplished by monitoring a patient's conditions during drug treatment. By using the systems and methods of the present invention before, during and after different drug treatments, the most efficacious drug for an individual patient can be selected.

Figure 6:
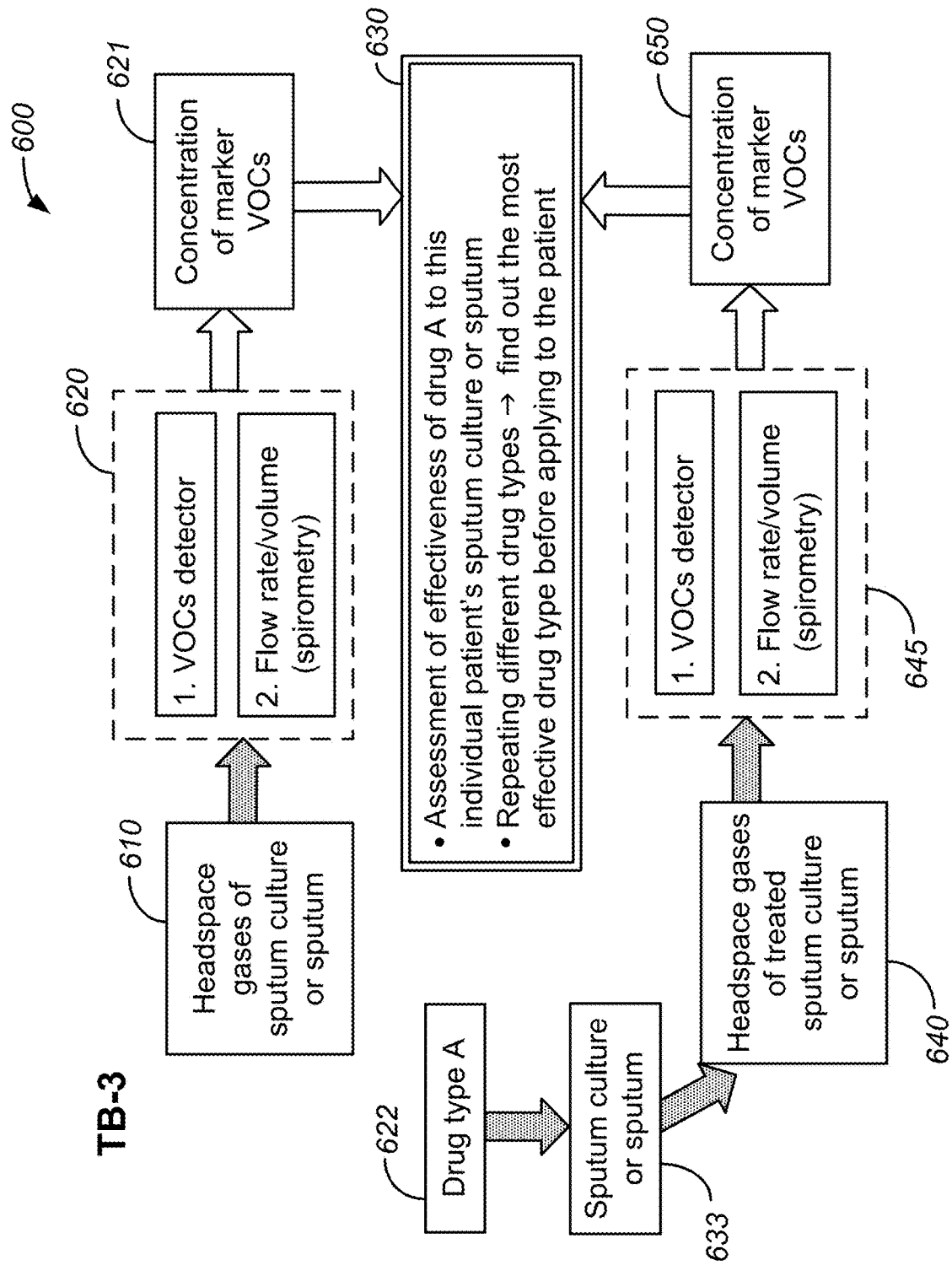
FIG. 6 illustrates one embodiment of the invention for the detection and monitoring of TB.

Turning now to FIG. 6, yet another embodiment 600 of the present invention is illustrated. As shown therein, headspace gases of sputum culture, or breath is assessed 610 via the analyzer 620 and the concentration of marker VOCs 621 is determined. Advantageously, various drugs can be used 622 in order to assess their efficacy on the particular bacterium in the sputum or sputum culture 633. The headspace gases 640 are analyzed via the analyzer 645 and the concentration of the biomarkers assessed 650. The systems and methods herein assess the effectiveness of drugs (e.g., drug A, 622) to an individual patient's sputum, or sputum culture. The process can be repeated with different drug types (B-Z) to find the most efficacious drug 630. This embodiment also contemplates the use of the disclosed systems and methods in clinical trials and drug research.

Figure 7:
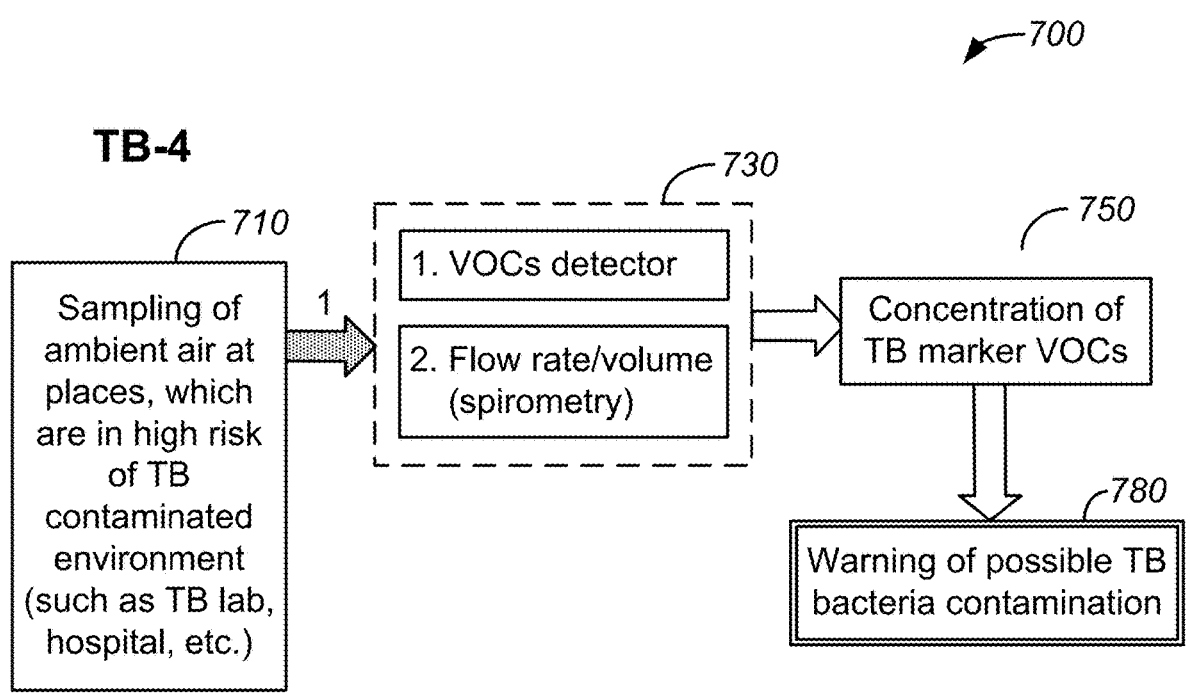
FIG. 7 illustrates one embodiment of the invention for the detection and monitoring of TB.

FIG. 7 illustrates another embodiment 700 of the present invention. As shown therein, sampling of ambient air can be carried out at various places, which are high risk for TB contaminated environments such as TB labs, hospitals, clinics, health care facilities, nursing homes, jails, prisons, and the like 710. The analyzer 730 assesses the concentration of various concentration of VOCs 750. If the VOCs are above a threshold value, a warning is communicated 780.

In certain instances, the following are VOCs useful for TB detection: 1-methyl-naphthalene, 3-heptanone, methylcyclododecane, 2,2,4,6,6-pentamethyl-heptane, 1-methyl-4-(1-methylethyl)-benzene, 1,4-dimethylcyclohexane, 1,3-isobenzofurandione, 2,3-dimethyl-pentane, acetaldehyde, α,α, dimethylbenzenemethanol, cyclohexane, 2,2'-diethyl-1,1'-biphenyl, and 2,3-dihydro-1,1,3-trimethyl-3-phenyl-1H-indene. Others include, but are not limited to, trans 1,3-dimethyl-cyclohexane, 1,4-dichloro-benzene, 1-octanol, 2-butanone, camphene, 4-methyl-decane, 3-ethyl-2-methyl-heptane, 2,6-dimethyloctane, 1,2,3,4-tetramethylbenzene, trans-3,6,6-trimethyl-bicyclo-3-1-1-hept-2-ene, trans 1-ethyl-4-methyl-cyclohexane, and 1-β-pinene.

Furthermore, the application can also be applied to bench-top or central-lab instruments, such as GC/MS, or an electronic nose. The methods and systems disclosed herein allow for very high sensitivity and specificity for TB tests based on the patients' exhaled VOCs and headspace gases of cultured microbacteria.

Figure 8:
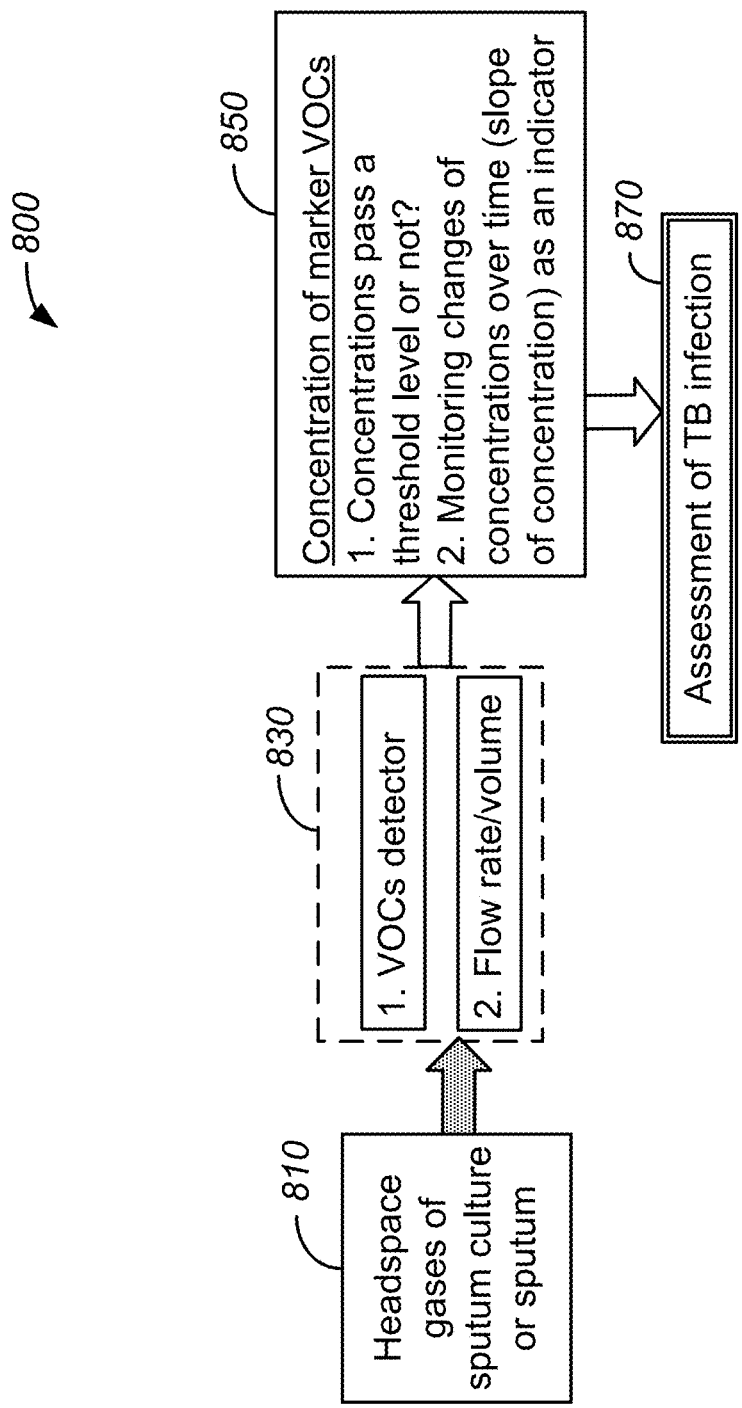
FIG. 8 illustrates one embodiment of the invention for the detection and monitoring of TB.

FIG. 8 illustrates yet another embodiment 800 of the present invention. As shown therein, the present invention provides devices and methods to sample a sputum culture such as the headspace 810 wherein an analyzer 830 assesses the concentration of various marker VOCs 850, or monitors the changes of VOCs concentrations over time (e.g., slope of concentration). The devices and methods allow for the assessment of a TB 870 infection by either VOCs passing a threshold, or for example, the slope exceeding a certain value. Various therapeutic compounds can be tested for being the most efficacious for the patient. In this manner, the medication therapy can be tailored to an individual patient (personalized device) through the testing of various antibiotics. This embodiments allows for the replacement of current TB diagnostic methods and is faster and more accurate.

C. Lung Cancer

In still other embodiments, the present invention provides methods and systems for the detection of whether a subject has lung cancer or monitoring a subject having lung cancer. In certain instances, the VOCs for lung cancer include, but are not limited to, 2-heptanone, 4-methyl-nonane, heptanal, 2-methyl-nonane, 1,1'-bicyclopentyl, nonane, 4-methyl-octane, hexanal, propyl-cyclohexane, trideuteroacetonitrile, 5-methyl-2-hexanamine, 1-butyl-2-methyl, cis-cyclopropane, 1,1,3-trimethyl-cyclohexane, 2-chloro-1-(difluoromethoxy)-1,1,2-trifluoro-ethane, 3-ethyl-2-methyl-heptane, 1,3-dimethyl-, trans-cyclohexane, 3-(methylthio)-1-propene, 3,6-dimethyl-octane, 2,3-dimethyl-pentane, chloroform, 1-(1-methyl-2-cyclopenten-1-yl)-ethanone, 2-cyano-acetamide, 4-(1,1-dimethylethyl)-cyclohexene, 1-methyl-4-(1-methylethenyl), cyclohexene, 1,1-dimethyl-cyclopropane, 2-methoxy-ethyl, acetate, 1-methyl-1-(1-methylethyl)hydrazine, trans-anti-1-methyl-decahydronaphthalene, ethynyl-benzene, 2-methylbutylidene-cyclopentane, octahydro 4,7-ethano-1H-indene, 5-methoxy-1-aza-6-oxabicyclo(3.1.0)hexane, 1,1-dimethylcyclohexane, 4-(1-methylethyl)-heptane, 1,4-dimethyl-cis-cyclohexane, pentanal, 3-methyl-nonane, 1,2,3-trimethyl-, (1α2β3α)cyclohexane, 2-β-pinene, [10B]-Triethylborane, 2,5-dimethyl-, cis-piperazine, delta-4-carene, 2-methyl-2-methylbutyl propanoic acid ester, 3-methyl-pentane and a combination thereof.

In certain aspects, the methods and systems described herein can diagnose the two main types of lung cancer, i.e., non-small cell lung cancer and small cell lung cancer. Non-small cell lung cancer (NSCLC) accounts for about 80% of lung cancers, these include, squamous cell carcinoma, adenocarcinoma, and bronchioalveolar carcinoma. Small cell lung cancer (SCLC) accounts for about 20% of all lung cancers.

III. Sensor Arrays

In certain aspects, the detector array comprises a sensor or a plurality of sensors. In one aspect, the sensors are surface micromachined sensors (MEMS). In other embodiments, the sensors can be bulk micromachined sensors, meaning that at least some of the MEMS sensors are formed within a substrate instead of on the surface. Still other embodiments of the sensor array using MEMS sensors can include combinations of surface-micromachined and bulk-micromachined sensors. Different types of sensors (not limited to MEMS types) can be used, depending on the application and the required sensitivity. Examples of MEMS sensors that can be used include chemiresistors, bulk acoustic wave (BAW) sensors, and the like. In other embodiments, the detector array comprises one or more of the sensors which can be a non-MEMS sensor. Examples of non-MEMS sensors that can be used in detector array include SAW (surface acoustic wave) sensors with quartz or gallium arsenide substrates or a QCM (quartz crystal microbalance).

In certain aspects, each sensor includes a surface with a coating thereon. Each coating used will have an affinity for one or more of the particular chemicals being detected e.g., (NO, VOCs), such that the coating absorbs or chemically interacts with its corresponding chemical or chemicals. The interaction between coating and chemical in turn changes a physical property of the sensor such as resonant frequency, capacitance or electrical resistance, and that changed physical property of the sensor can be measured using a transducer or other measurement device. In one aspect, a particular coating chosen for a sensor will depend on the chemicals that sensor array will be used to detect. The chemical affinity of coatings may also vary strongly with temperature, so that the operating temperature range should be considered in selecting coatings. In an embodiment where the sensor array will be used to detect volatile organic compounds in human breath—such as benzene, toluene, n-octane, ethylbenzene, m- or p-xylene, α-pinene, d-limonene, nonanal, benzaldehyde, 2-methylhexane, and 4-methyloctane. Coatings that can be used in different applications include amorphous copolymers of 2,2-bistrifluoromethyl-4, 5-difluoro-1,3-dioxole (PDD) and tetrafluoroethylene (TFE), PtCl2 (olefin), C8-MPN, and the like.

The number of sensors needed depends on the number of different chemicals to be detected, and on the nature of the coatings used on the sensors. In an embodiment where each coating absorbs or chemically interacts with only one chemical, the number of sensors can correspond exactly to the number of chemicals to be detected, but in other embodiments, it can be desirable to have a given coating on more than one sensor for redundancy. In one aspect, there is not a one-to-one correlation between chemicals to coatings. In other words, each coating reacts with more than one different chemical and the reaction between different chemicals and a given coating will vary in nature and strength. The detector array having sensors with different coatings is therefore useful because the response of the detector array can have different patterns for different gases.

IV. Signal Processing

In certain aspects, the signal analysis is via a neural network algorithm or learning algorithm. Pattern recognition using neural networks is well-established in the art. The neural network is trained with a training set and thereafter validated with a validation set.

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks.

Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for further descriptions of neural networks.

Ambient air is monitored for VOC stimulus warning and saved as baseline level. Both the inhaled and exhaled breathes are measured for flow rate and volume. The exhaled breath is collected and filtered by background data for NO and VOCs detection for asthma assessment.

V. EXAMPLES

Example 1

Figure 9A:
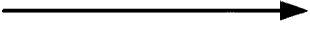

A clinical trial is conducted to differentiate grades of asthma severity as assessed according to the 2007 National Asthma Education and Prevention Program (NAEPP) guidelines. These guidelines are described in the National Heart, Lung, and Blood Institute NAEPP Expert Panel Report 3: Guidelines for the Diagnosis and Management of Asthma, Full Report 2007. Using the guidelines in Expert Panel Report 3 (see, FIGS. 9A-B) impairment and risk of 600 patients are assessed and classified into 1) Intermittent; 2) Mild; 3) Moderate; or 4) Severe. The Expert Panel Report 3 indicates that 153 individuals have Intermediate asthma; 101 individuals have Mild asthma; 256 are Moderate asthma and 90 are Severe asthma.

After the severity of each patient's asthma is classified according to the 2007 NAEPP guidelines, breath samples from the 600 asthma patients are obtained. Levels of nitric oxide and volatile organic components (VOC), including the compounds 4-methyloctane, 2,4-dimethylheptane, isopropanol, toluene, isoprene, alkane, acetic, acetone, 2,6,11-trimethyl dodecane, 3,7-dimethyl undecane, and 2,3-dimethyl heptanes as examples, are measured. The baseline level of the markers in the ambient air is determined, and the breath sample levels are adjusted by the baseline level of the markers in the ambient air.

Using these breath samples for each classification, VOCs and NO levels are determined. A cohort of these samples (300) is used as a training data set of the sensor array, which serves as a basis, model, or template against which the features of an unknown sample are compared, in order to classify the unknown disease state of the sample. Once trained, the sensor array is then validated with a cohort (300) of samples that had not been used in the training set. This is known as the validation set. The data obtained from this test is used to calculate all accuracy parameters for the sensor array.

In addition to the foregoing marker training, spirometry data of each of the 600 patients is performed to measure forced expiratory volume in 1 second ($FEV_1$), both before and after administration of a bronchodilator. The spirometry data is added to the training set and validation set using data analysis software. The sensitivity, specificity, and accuracy of the sensor array is calculated.

Figure 10A:
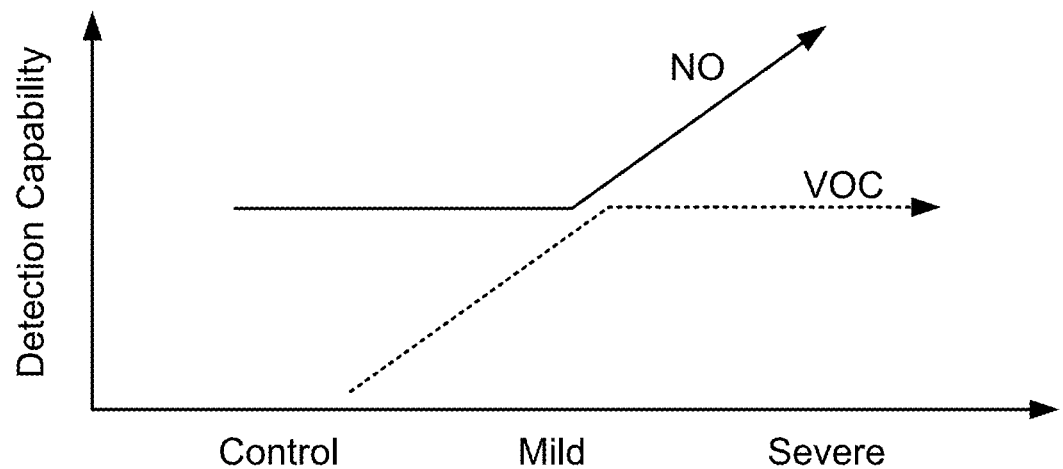
FIG. 10A-B illustrate one embodiment for the detection of asthma wherein VOCs are useful for the detection and diagnosis of "no asthma or mild asthma" (Panel A); and NO is useful for the detection of mild and severe asthma (Panel B).
Figure 10B:
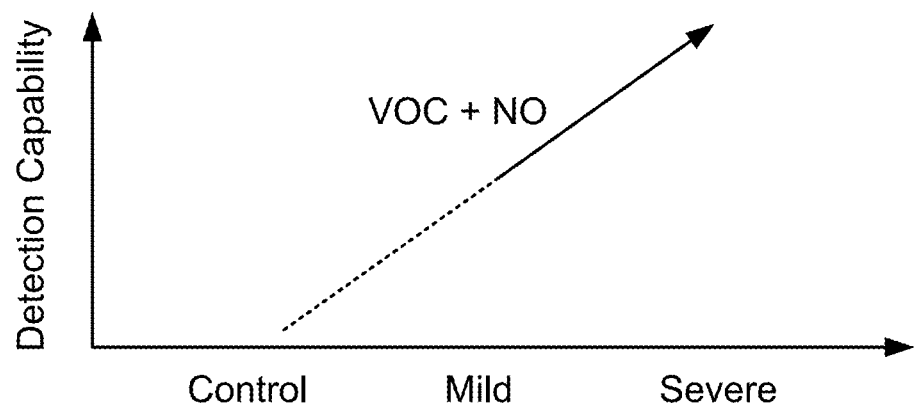

As is illustrated in FIG. 10A-B, the methods herein increase specificity and the dynamic range of monitoring severity of asthma by detecting all VOCs, NO, and flow rate or any one of the foregoing. Preferably, the systems and methods herein monitor VOCs for patients with mild or no asthma, whereas for mild or sever asthma, NO levels are quantitated.

Example 2

Breath samples from 150 asthma patients and 50 non-asthmatic healthy controls are obtained. As described in Example 1, marker levels are measured, and spirometry is performed. Using the trained and validated sensor array, 150 asthma patients can be classified by degree of severity.

Using the trained sensor array, the asthma severity level is predicted for each of 200 patients. The asthma severity level of each of the 150 patients is thereafter classified by the 2007 NAEPP guidelines, and the results are compared. The sensitivity, specificity, and accuracy of the algorithm is compared to the results of Example 1.

Example 3

A sensor array is developed to identify tuberculosis infection by measurement of VOC levels in a patient's breath, sputum and sputum culture.

Breath and sputum samples from 200 patients with active tuberculosis, 200 patients with latent tuberculosis, and 100 healthy controls are obtained. A definitive diagnosis of tuberculosis is made by culturing *Mycobacterium tuberculosis* organisms from a specimen taken from each patient.

Levels of the markers of volatile organic components (VOC) including off-gasses from *Mycobacterium tuberculosis* or *Mycobacterium bovis* are measured from specimens from each of the 500 patients. The results are adjusted by the concentration of the markers in the ambient air. Using these samples for each classification, VOCs are determined. A cohort of these samples (200) is used as a training data set of the sensor array, which serves as a basis, model, or template against which the features of an unknown sample are compared, in order to classify the unknown disease state of the sample. Once trained, the sensor array is then validated with a cohort (200) of samples that had not been used in the training set. The data obtained from this test is used to calculate all accuracy parameters for the sensor array. The sensitivity, specificity, and accuracy of the sensor array is calculated.

Example 4

Breath samples from 100 patients with active tuberculosis, 100 patients with latent tuberculosis, and 50 healthy controls are obtained. The presence and severity of tuberculosis in each patient is identified by conventional screening techniques. As described in Example 3, marker levels are measured.

Using the algorithm defined in Example 3, the tuberculosis classification is calculated for each patient, and the results are compared with the tuberculosis classification of each patient as identified by standard screening techniques. The sensitivity, specificity, and accuracy of the sensor array is compared to the results of Example 3.

Example 5

Breath samples from 87 patients with active tuberculosis are obtained. The presence and severity of tuberculosis in each patient is verified using the IS 6110 repetitive DNA element of *Mycobacterium tuberculosis*. Before treatment, the breath VOCs are collected from each patient. Various drugs are used to treat TB including isoniazid, rifampin (brand name: Rifadin), ethambutol (brand name: Myambutol) and pyrazinamide. The patients take their medicine as directed. During treatment, breath samples show the patients will be better and feel healthier. VOCs from breath samples verify that patients are better. After treatment, the VOCs verify that TB infection is no longer present.

In a concurrent analysis, a sputum is cultured for each of the 87 patients. Headspace gases of each sputum culture is assessed via the analyzer and the concentration of marker VOCs is determined. The same drugs are used in order to assess their efficacy on the particular bacterium in the sputum culture. The methods assess the effectiveness of the drugs to find the most efficacious drug.

Example 6

This example represents a clinical trial with 87 patients. Breath samples from 87 patients are obtained in a Phase I study. VOC markers of TB Mycobacteria are validated. The protocol includes collecting headspace of (1) TB cultures, (2) NTM cultures, (3) microbial flora in oral cavity and respiratory track, and (4) control tubes. It is then possible to identify specific VOC markers of TB culture headspace and is optimized.

In Phase II, the VOC markers from patient's breath are verified and the clinical trial protocol is established. The protocol includes collecting clinical samples—both sputum & breath—from patient and control; repeating phase-I in-vitro tests on sputum sample as reference; identifying specific VOC markers of TB patient breath.

In Phase III, cross-site clinical trials for optimization.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting whether a subject has a respiratory disease or monitoring a subject with a respiratory disease said method comprising:
   receiving, at a portable apparatus having a gas chromatograph coupled to a detector array, ambient air to be inhaled by said subject, wherein the portable apparatus includes the gas chromatograph and the detector array replaceably mounted to a substrate of the portable apparatus;
   filtering, by a volatile organic compound (VOC) filter, the ambient air to remove at least a portion of background VOC content in the ambient air;
   further filtering, by a nitric oxide (NO) filter, the ambient air to remove at least a portion of background NO content from the ambient air;
   providing, at the portable apparatus, at least a portion of the ambient air to said subject to be inhaled;
   receiving, at the portable apparatus, breath exhaled from said subject;
   contacting the breath exhaled from said subject with the gas chromatograph mounted to the substrate of the portable apparatus;
   producing, by the detector array coupled to the gas chromatograph and mounted to the substrate of the portable apparatus, an indicator based on the exhaled breath from said subject, the indicator being produced based at least in part on one or more analytes in the breath exhaled from said subject, and the indicator being indicative of one or more biomarkers in the exhaled breath; and
   analyzing, by an analysis circuit disposed on said portable apparatus, said indicator to determine whether said subject has asthma, wherein the determination is made based on an NO concentration level in conjunction with VOC detection from the breath exhaled from said subject.

2. The method of claim 1, wherein analyzing said produced indicator includes determining a severity level of the asthma.

3. The method of claim 1, further comprising:
   detecting whether the exhaled breath of said subject contains NO or VOCs.

4. The method of claim 1, wherein said VOC is one of a group consisting of 4-methyloctane, 2,4-dimethylheptane, isopropanol, toluene, isoprene, alkane, acetic, acetone, 2,6,11-trimethyl dodecane, 3,7-dimethyl undecane, 2,3-dimethyl heptane and a combination thereof.

5. The method of claim 1, further comprising:
   obtaining, by the portable apparatus, periodic breath samples to monitor an efficacy of a therapeutic.

6. The method of claim 1, wherein the portable apparatus further includes a spirometer and a preconcentrator mounted thereon, and wherein the method further comprises:
   measuring or controlling, by the spirometer, a volume and speed of airflow from the breath of said subject; and
   increasing, by the preconcentrator, a concentration of the one or more analytes in the breath exhaled from said subject.

7. The method of claim 6, wherein exhaled breath from said subject includes a flow rate, and wherein the spirometer adjusts the flow rate of the exhaled breath.

8. The method of claim 1, wherein the breath exhaled from said subject is received via a ventilator in fluid communication with a lung of said subject.

9. The method of claim 6, wherein said preconcentrator contains a substance having affinity for NO and VOCs.

10. The method of claim 1, further comprising:
    monitoring, by the portable apparatus, the ambient air;
    presenting an environmental warning to said subject when a baseline concentration level of the background VOC content in the ambient air is above a threshold level.

11. The method of claim 1, further comprising:
determining a baseline concentration level of both background NO content and background VOC content in the ambient air; and
saving the baseline concentration level, wherein the indicator is produced by subtracting the baseline concentration level from output data associated with breath exhaled from said subject.

12. The method of claim 1, wherein said detector array comprises a MEMS sensor array.

13. The method of claim 1, wherein the produced indicator is analyzed via a pattern recognition algorithm.

14. The method of claim 1, wherein said detector array is removable and replaceable.

15. The method of claim 6, wherein said preconcentrator and the gas chromatograph are disposable.

16. The method of claim 15, wherein said portable apparatus further comprises a mouthpiece, and wherein the mouthpiece is removable, replaceable, and disposable.

17. The method of claim 1, wherein analyzing the produced indicator includes determining a level of the one or more biomarkers present in the breath from said subject.

18. The method of claim 1, wherein the detector array includes at least one of an acoustic resonator or a resistive sensor with a surface coating, wherein the surface coating is capable of absorbing or chemically interacting with one or more biomarkers present in the exhaled breath.

19. The method of claim 1, further comprising:
providing a quantitative assessment of asthma based on the analysis of the produced indicator.

20. The method of claim 1, wherein the breath exhaled from the subject is associated with a fluid, and wherein the method further comprises:
separating, by the gas chromatograph on the portable apparatus, individual chemicals in the fluid in a time domain such that different chemicals are separately outputted by the gas chromatograph across time, wherein the indicator is produced based on the individual chemicals in the fluid.

21. A portable apparatus comprising:
a substrate;
a volatile organic compound (VOC) filter configured to filter ambient air received at the portable apparatus to remove at least a portion of background VOC content in the ambient air;
a nitric oxide (NO) filter configured to further filter the ambient air to remove at least a portion of background NO content from the ambient air prior to the ambient air being inhaled by a subject;
a gas chromatograph replaceably mounted on the substrate, the gas chromatograph configured to receive a fluid associated with breath exhaled from a subject and separates individual chemicals in the fluid;
a preconcentrator configured to increase a concentration of one or more analytes in the breath exhaled from said subject;
a detector array replaceably mounted on the substrate, the detector array configured to receive the individual chemicals from the gas chromatograph and produces an indicator based on the received individual chemicals, the indicator being produced based at least in part on the one or more analytes in the breath exhaled from said subject, and the indicator being indicative of one or more biomarkers in the exhaled breath; and
an analyzer configured to analyze the produced indicator and determine an NO concentration level in conjunction with one or more VOCs from the breath exhaled from said subject.

22. The apparatus of claim 21, wherein the gas chromatograph separates individual chemicals in the fluid in a time domain such that different chemicals are separately outputted by the gas chromatograph across time.

23. The method of claim 6, wherein the one or more analytes in the breath exhaled from said subject includes one or more VOCs, wherein the preconcentrator includes an adsorbent material that has an affinity for one or more VOCs, and wherein increasing the concentration of the one or more analytes includes heating the preconcentrator to desorb the one or more VOCs.

24. The apparatus of claim 21, wherein the portable apparatus further includes one or more sockets mounted to the substrate, and wherein the detector array and the gas chromatograph are mounted to the substrate via the one or more sockets mounted to the substrate.

25. The apparatus of claim 24, wherein the substrate is a printed circuit board, and wherein the one or more sockets includes a zero insertion force (ZIF) socket.

26. The method of claim 1, wherein the gas chromatograph and the detector array are replaceably mounted to the substrate of the portable apparatus via one or more sockets of the substrate, wherein the substrate is a printed circuit board, and wherein the one or more sockets includes a zero insertion force (ZIF) socket.

27. A method for detecting whether a subject has a respiratory disease or monitoring a subject with a respiratory disease said method comprising:
receiving, at a handheld apparatus having a gas chromatograph coupled to a detector array, breath exhaled from said subject, wherein the handheld apparatus includes the gas chromatograph and the detector array replaceably mounted to a substrate of the handheld apparatus;
increasing, by a preconcentrator on the handheld apparatus, a concentration of one or more analytes in the breath exhaled from said subject;
contacting the increased concentration of the one or more analytes with the gas chromatograph mounted to the substrate of the handheld apparatus;
producing, by the detector array on the handheld apparatus, an indicator based on the exhaled breath from said subject, the indicator being produced based at least in part on the one or more analytes in the breath exhaled from said subject, and the indicator being indicative of one or more biomarkers in the exhaled breath; and
analyzing, by an analysis circuit disposed on said handheld apparatus, said produced indicator to determine whether said subject has the respiratory disease, wherein the determination is made based on an NO concentration level in conjunction with VOC detection from the breath exhaled from said subject.

28. The method of claim 27, further comprising:
determining a level of background VOC content; and
communicating a warning alert to the subject when the level of background VOC content exceeds a threshold level.

* * * * *